(12) United States Patent
Harrewijn et al.

(10) Patent No.: US 8,779,234 B2
(45) Date of Patent: *Jul. 15, 2014

(54) **RESISTANCE TO DOWNY MILDEW OF ONION CAUSED BY THE FUNGUS *PERONOSPORA DESTRUCTOR***

(75) Inventors: Jan Leendert Harrewijn, Noord-Scharwoude (NL); Joannes Petrus Hubertus Hoogenboom, Tuitjenhorn (NL)

(73) Assignee: Nickerson Zwaan B.V., Made (NL)

( * ) Notice: Subject to any disclaimer, the term of this patent is extended or adjusted under 35 U.S.C. 154(b) by 5 days.

This patent is subject to a terminal disclaimer.

(21) Appl. No.: 13/240,493

(22) Filed: Sep. 22, 2011

(65) Prior Publication Data

US 2012/0017331 A1 Jan. 19, 2012

Related U.S. Application Data

(63) Continuation of application No. 11/811,120, filed on Jun. 7, 2007, now Pat. No. 8,119,856, which is a continuation of application No. PCT/EP2005/013537, filed on Nov. 25, 2005.

(30) Foreign Application Priority Data

Dec. 8, 2004 (EP) .................................. 04078320

(51) Int. Cl.
| | | |
|---|---|---|
| *A01H 1/00* | (2006.01) | |
| *A01H 1/02* | (2006.01) | |
| *A01H 5/00* | (2006.01) | |
| *C12N 5/04* | (2006.01) | |

(52) U.S. Cl.
USPC ........... 800/267; 800/260; 800/278; 800/298; 800/266; 800/279; 435/468

(58) Field of Classification Search
USPC .......... 800/260, 267, 279, 301, 298; 435/468, 435/410
See application file for complete search history.

(56) References Cited

U.S. PATENT DOCUMENTS 8,119,856 B2 2/2012 Harrewijn et al.

OTHER PUBLICATIONS

Hildebrand, P.D. et al. (1980) "Maintenance of *Personospora destructor* in onion sets", *Canadian Journal of Plant Pathology* 2:239-240.
Kalkman, E.R. (1984) "Analysis Of The C-banded Karotype Of *Allium cepa* L. Standard System Of Nomenclature And Polymorphism", *Genetica* 65:141-148.
Khrustaleva, L.I. and Kik, C. (1998) "Cytogenetical Studies I The Bridge Cross *Allium cepa* L.* (*A. fistulosum* *A. cepa*)", *Theor. Appl. Genet.* 96:8-14.
Khrustaleva, L.I, and Kik, C. (2000) "Introgression Of *Allium fisulosum* Into *A. cepa* Mediated By *A. roylei*", *Theor. Appl. Genet.* 100:17-26.
Kofoet, A. et al. (1990) "Inheritance Of Resistance To Downy Mildew (*Peronospora destructor* [Berk.]Casp.) From *Allium roylei* Stearn In The Backcross *Allium cepa* L.* (*A. royeli*A. cepa*)", *Plant Breeding* 105:144-149.
Meer, Q.P. van der and Vries, J.N. (1990) "An Interspecific Cross Between *Allium roylei* Stearn And *Allium cepa* L. And Its Backcross To *A. cepa*", *Euphytica* 47:29-31.
Michelmore, R.W. et al. (1991) "Identification Of Markers Linked To Disease-Resistance Genes By Bulked Segregant Analysis: A Rapid Method To Detect Markers In Specific Genomic Regions By Using Segregating Populations", *Proc. Natl. Acad. Sci. USA* 88:9828-9832.
Mukerji, K.G. (1975) "*Peronospora destructor*" *CMI Description Of Pathogenic Fungi And Bacteria* No. 456.
Rogers, S.O. and Bendich, A.J. (1988) "Extraction Of DNA From Plant Tissues" In: Gelvin SB, Schilperoort RA (eds) Plant Molecular Biology Manual A6, Kluwer Academic Publ., Dordrecht, the Netherlands, pp. 1-10.
Van Heusden, A.W. et al. (2000) "A Genetic Map Of An Interspecific Cross in *Allium* Based On Amplified Fragment Length Polymorphism (AFLP™) Markers", *Theor. Appl. Genet.* 100:118-126.
Viranyi, F. (1981) "Downy Mildew Of Onion" *DM Spencer, The Downy Mildews.* Chapter 21, pp. 461-471.
Vos, P. et al (1995) "AFLP: A New Technique for DNA Fingerprinting", *Nucleic Acids Research* 21:4407-4414.
Vries, J.N. De et al. (1992) "Linkage Of Downy Mildew Resistance Genes $Pd_1$ and $Pd_2$ From *Allium roylei* Stearn In Progeny Of Its Interspecific Hybrid With Onion (*A. cepa* L.)", *Euphytica* 64:131-137.
Vries, J.N. De (1990) "Onion Chromosome Nomenclautre And Homoeology Relationships Workshop Report", *Euphytica* 49:1-3.
PCT International Search Report issued Feb. 9, 2006 in connection with PCT International Application No. PCT/EP2005/013537.
Scholten, O.E. (2007) "The long and winding road leading to the successful introgression of downy mildew resistance into onion", *Euphytica*, 156, pp. 345-353.

(Continued)

*Primary Examiner* — Medina A Ibrahim

(74) *Attorney, Agent, or Firm* — John P. White; Cooper & Dunham LLP

(57) ABSTRACT

The present invention relates to plants of the *Allium cepa* species, which are resistant to the downy mildew of onion caused by the fungus *Peronospora destructor*, due to a Pd resistance locus, wherein any fragment of a chromosome, comprising the Pd resistance locus, can be present homozygously in progeny without causing lethality. The present invention also encompasses plants of the *Allium cepa* species which are resistant to downy mildew of onion caused by the fungus *Peronospora destructor* (Pd) due to Pd resistance locus present homozygously in the genome of the plants. The present invention also provides processes for obtaining plants resistant to downy mildew of onion, which are suitable for obtaining cultivated onions and shallots.

21 Claims, 5 Drawing Sheets

(56) References Cited

OTHER PUBLICATIONS

International Search Report issued by the International Searching Authority (ISA/EP) on Feb. 23, 2006 in connection with the International Application No. PCT/EP2005/013537.
Written Opinion Of the International Searching Authority issued by the International Searching Authority (ISA/EP) on Feb. 23, 2006 in connection with the International Application No. PCT/EP2005/013537.
Requirement for Restriction/Election issued Jun. 24, 2009 in connection with U.S. Appl. No. 11/811,120.
Office Action issued Mar. 17, 2010 in connection with U.S. Appl. No. 11/811,120.
Office Action issued Mar. 28, 2011 in connection with U.S. Appl. No. 11/811,120.
Notice of Allowance and Fees Due issued Oct. 18, 2011 in connection with U.S. Appl. No. 11/811,120.
Sep. 21, 2010 Amendment in Response to Mar. 17, 2010 Office Action in connection with U.S. Appl. No. 11/811,120.
Jun. 23, 2011 Amendment in Response to Mar. 28, 2011 Office Action in connection with U.S. Appl. No. 11/811,120.
Van Heusden et al., "AFLP linkage group assignment to the chromosomes of *Allium cepa* L. via monosomic addition lines," Theor Appl Genet (2000) 100: 480-486.

SEQUENCE LISTING

<160> NUMBER OF SEQ ID NOS: 12

<210> SEQ ID NO 1
<211> LENGTH: 21
<212> TYPE: DNA
<213> ORGANISM: Artificial
<220> FEATURE:
<223> OTHER INFORMATION: adapter alpha

<400> SEQUENCE: 1
ctcgtagact gcgtacatgc a                    21

<210> SEQ ID NO 2
<211> LENGTH: 14
<212> TYPE: DNA
<213> ORGANISM: Artificial

```
<220> FEATURE:
<223> OTHER INFORMATION: adapter alpha

<400> SEQUENCE: 2
tgtacgcagt ctac                                                        14

<210> SEQ ID NO 3
<211> LENGTH: 16
<212> TYPE: DNA
<213> ORGANISM: Artificial
<220> FEATURE:
<223> OTHER INFORMATION: adapter beta

<400> SEQUENCE: 3
gacgatgagt cctgag                                                      16

<210> SEQ ID NO 4
<211> LENGTH: 14
<212> TYPE: DNA
<213> ORGANISM: Artificial
<220> FEATURE:
<223> OTHER INFORMATION: adapter beta

<400> SEQUENCE: 4
tactcaggac tcat                                                        14

<210> SEQ ID NO 5
<211> LENGTH: 19
<212> TYPE: DNA
<213> ORGANISM: Artificial
<220> FEATURE:
<223> OTHER INFORMATION: primer A

<400> SEQUENCE: 5
gactgcgtac atgcagaac                                                   19

<210> SEQ ID NO 6
<211> LENGTH: 19
<212> TYPE: DNA
<213> ORGANISM: Artificial
<220> FEATURE:
<223> OTHER INFORMATION: primer A

<400> SEQUENCE: 6
gatgagtcct gagtaactt                                                   19

<210> SEQ ID NO 7
<211> LENGTH: 19
<212> TYPE: DNA
<213> ORGANISM: Artificial
<220> FEATURE:
<223> OTHER INFORMATION: primer B

<400> SEQUENCE: 7
gactgcgtac atgcagaag                                                   19

<210> SEQ ID NO 8
<211> LENGTH: 19
<212> TYPE: DNA
<213> ORGANISM: Artificial
<220> FEATURE:
<223> OTHER INFORMATION: primer B

<400> SEQUENCE: 8
gatgagtcct gagtaaaac                                                   19
```

```
<210> SEQ ID NO 9
<211> LENGTH: 19
<212> TYPE: DNA
<213> ORGANISM: Artificial
<220> FEATURE:
<223> OTHER INFORMATION: primer C

<400> SEQUENCE: 9
gactgcgtac atgcagaca                                            19

<210> SEQ ID NO 10
<211> LENGTH: 19
<212> TYPE: DNA
<213> ORGANISM: Artificial
<220> FEATURE:
<223> OTHER INFORMATION: primer C

<400> SEQUENCE: 10
gatgagtcct gagtaacca                                            19

<210> SEQ ID NO 11
<211> LENGTH: 19
<212> TYPE: DNA
<213> ORGANISM: Artificial
<220> FEATURE:
<223> OTHER INFORMATION: primer C'

<400> SEQUENCE: 11
gactgcgtac atgcagaaa                                            19

<210> SEQ ID NO 12
<211> LENGTH: 19
<212> TYPE: DNA
<213> ORGANISM: Artificial
<220> FEATURE:
<223> OTHER INFORMATION: primer C'

<400> SEQUENCE: 12
gatgagtcct gagtaacac                                            19
```

RESISTANCE TO DOWNY MILDEW OF ONION CAUSED BY THE FUNGUS *PERONOSPORA DESTRUCTOR*

The present application is a continuation of U.S. Ser. No. 11/811,120 filed Jun. 7, 2007 now U.S. Pat. No. 8,119,856, which is a continuation of PCT International Application No. PCT/EP2005/013537, filed Nov. 25, 2005, and claims priority of European Patent Application No. 04078320.1, filed Dec. 8, 2004, the contents of all of which are hereby incorporated by reference into this application.

The present invention relates to plants of the genus *Allium* which are resistant to the downy mildew of onion caused by the fungus *Peronospora destructor* (Pd) (Berk.) Cas., specifically plants of the *Allium cepa* or *Allium fistulosum* species. According to the invention, the resistance is provided by a resistance locus, which can be present homozygously or heterozygously in the genome of the plant, and which is sufficient to provide resistance to plants bearing this locus. The present invention also provides processes for obtaining said plants resistant to downy mildew of onion, said processes being suitable for obtaining cultivated onions and shallots.

BACKGROUND OF THE INVENTION

Downy mildew caused by the fungus *Peronospora destructor* (Pd) is practically world-wide in distribution. The pathogen attacks various kinds of onions, but is especially destructive to the common onion *Allium cepa*. The damage caused by the fungus is described in Mukerji (ref 5). Spontaneous epidemics may occur in the field, if conditions are favourable for the disease. The symptoms are yellowing of the leaves and grey sporulation.

From an economical point of view, downy mildew is one of the major fungal diseases threatening the cultivation of onions and shallots (*Allium cepa* L.), almost in all onion-growing regions in the world.

It is assumed that no complete natural resistance to downy mildew is present in *Allium cepa* and *Allium fistulosum*. However, a complete resistance to downy mildew was found in the wild *Allium roylei* Stearn. Inspired by a certain morphological resemblance between *A. roylei* and *A. cepa* it has therefore been proposed to use *A. roylei* as an introgression partner for *A. cepa*. In the publication by van der Meer and de Vries (ref 1) preliminary results are reported concerning such a hybrid between *A. roylei* and *A. cepa*, as well as results concerning the backcross of the interspecific hybrid to *A. cepa*. It has been observed that said interspecific hybrid is male and female fertile (Kofoet et al, ref 2). It has also been reported that a downy mildew resistance can be dominantly inherited in the BC1 (first backcross) progeny of this hybrid to onion.

The locus in the *cepa* genome, where the introgressed sequences responsible for the resistance are found, has been termed "Pd resistance locus". By extension, "Pd resistance locus" also designates the sequences themselves.

However, segregation for downy mildew resistance among BC1 and F2 progenies from the F1 between *A. roylei* and *A. cepa* is observed (de Vries et al, ref 3) and no breeding onion varieties resistant to downy mildew have ever been obtained, more than 10 years after the first resistant hybrid was obtained.

There is thus great interest from an agronomical and economical point of view for plants of *Allium cepa* and *Allium fistulosum* species, which are resistant to downy mildew and which are still 100% resistant after self-pollination i.e. there is no segregation of the resistance characteristic. These plants are particularly valuable as they may indeed be crossed with a susceptible line, giving hybrids which are also resistant to downy mildew of onion.

The invention lies first in the observation that all available resistant material of the *Allium cepa* and *Allium fistulosum* species was in fact heterozygous for the Pd resistance sequences and that no homozygous resistant plants have been obtained or disclosed in a reproducible manner up to now.

The present inventors elucidated the reason for which no homozygously resistant plant could be obtained and then succeeded in obtaining such *Allium* plants, which gives rise to progeny after self-pollination which is also 100% resistant (i.e. a homozygously resistant plant).

Several hypotheses could have explained the striking finding that no homozygous plants were available: translocation, recombination, hybrid preference selection, gene silencing and pleiotropic effects, linkage drag, etcetera . . . .

The present inventors have determined that the introgression fragment of *Allium roylei* which is present in the *cepa* hybrid and confers resistance to downy mildew comprises also a sequence designated "lethal factor", whose presence on both homologues of chromosome in *cepa* is lethal to the plant. For a resistant *cepa* plant to exist and grow, the introgression fragment, conferring resistance and containing the lethal factor, is thus necessarily present on a single chromosome homologue, explaining the absence of obtained homozygously resistant plants by the predecessors. This sequence responsible for lethality is present in the vicinity of the Pd resistance locus.

Having identified that the sequence conferring resistance is linked to a lethal sequence, the present inventors have succeeded, for the first time, in physically separating the sequence conferring resistance from the sequence responsible for lethality when present on both chromosomes.

This step of separation, which can be brought about by a recombination event, is the key point of the present invention. Indeed it could not be foreseen that the sequences conferring resistance could be separated from the lethal factor. First of all, it was not known whether said factor was a sequence which in itself was lethal or whether lethality arose as a result of the replacement, by sequences present on an introgression fragment, of endogenous essential sequences. Indeed, it is possible that the lethality is in fact a knock out of essential gene(s) on the corresponding *cepa*-fragment, which are not compensated by the fragment introduced from *A. roylei*. Therefore, different scenarios were possible to explain lethality:

the resistance sequences might have constituted in fact the lethal factor, because they replace endogenous critical sequences. They could thus never be present on both chromosomes without causing lethality.

the resistance sequences and the lethal sequences might have been extremely near to each other on the chromosome, or even overlapping. In this situation, the probability of obtaining a recombination event separating both is negligible.

the sequences constituting the lethal factor might have been necessary for the functioning of the resistance. In this condition, separating both would lead to the loss of the capacity for resistance.

In this context, the present inventors have unexpectedly succeeded in separating the sequences conferring the resistance phenotype from the sequence whose presence on both homologues is lethal.

The inventors have also found that the already released resistant *A. cepa* possess both the Pd resistance locus (which is dominant) and the lethal factor (which is recessively inherited) on the same introgression fragment. As the Pd resistance locus is dominant, the phenotype of the plant is "resistant" and the recessive lethal factor is not observed. However, progeny of such plants when crossed with susceptible plants will segregate and thus cannot be used commercially. Indeed, commercial onions and shallots are generally varieties, thus plant material, whether lines or hybrids, with a phenotype which has to be uniform; segregating traits of interest cannot be envisaged for commercial plants.

The present invention thus provides plants of the *Allium cepa* and *Allium fistulosum* species which are resistant to downy mildew of onion caused by *Peronospora destructor* (Pd) due to the presence in their genome of a Pd resistance locus, and said plants are homozygously resistant plants, i.e. plants which give a progeny after selfing which is also 100% resistant.

The present invention also provides resistant plants which can be obtained by crossing the above-mentioned resistant plants of the *Allium cepa* or *Allium fistulosum* species with a plant also of the *Allium cepa* or *Allium fistulosum* species which is susceptible to downy mildew.

The present invention also provides processes for obtaining said plants.

DETAILED DESCRIPTION OF THE INVENTION

Definitions

In the context of the present application, the following terms are defined in the following manner:

Introgression: natural introduction of genes of one species into another through the process of interspecific hybridization followed by successive backcrosses to the recurrent parents. Each species may thereby become more variable and show certain characters of the other species.

Pd resistance locus: Place in the chromosome occupied by the sequences responsible for resistance to *Peronospora destructor*, said sequences being sufficient to confer resistance to a plant. A Pd resistance locus may contain one gene or several genes, possibly separated by unrelated sequences or genes. By extension, in the context of the present invention, the sequences themselves are also called Pd resistance locus.

A possible Pd resistance locus is the introgression fragment of *A. Roylei* in the genome of a plant of the line 3591-1. Seeds of *Allium cepa* 3591-1 were deposited on Oct. 13, 2004 with NCIMB Ltd., Ferguson Building, Craibstone Estate, Bucksburn, Aberdeen, AB21 9YA, Scotland, under the provisions of the Budapest Treaty on the International Recognition of A Deposit For Purposes of Patent Procedure. NCIMB Ltd. assigned Accession Number NCIMB 41249 to this deposit.

Susceptible/susceptibility: according to the International Seed Federation, Section Vegetables, Position Paper of May 2004, in "Definition of the Terms Describing the Reaction of Plants to Pests or Pathogens for the Vegetable Seed Industry", susceptibility is the inability of a plant variety to restrict the growth and development of a specified pest or pathogen. It must however be noted that the term "sensitive" has also been widely used in the past decades for describing the same property.

By contrast, a plant which is able, to a certain extent and when compared to susceptible plant varieties under similar environmental conditions and pest or pathogen pressure, to restrict the growth and development of a specified pest or pathogen is qualified as resistant to said specified pest or pathogen. Resistant plants include plants which are tolerant, i.e. remain infected but survive, and plants which are totally resistant. Although being resistant to a pest or pathogen, a resistant plant attacked by said pest or pathogen may display symptoms characteristic of the infections, like reduced growth, earlier death, loss of leaves . . . .

Inbred line: nearly homozygous line (for all characters) produced by continued inbreeding and selection.

Homozygously resistant plant to a pathogen: plant which gives a progeny after selfing (self-pollination) which is also 100% resistant to said pathogen. Where the resistance is due to the presence of a DNA sequence in a chromosome of the plant, said sequence is present on all the homologues of the chromosome.

Lethal factor: factor, for example a genetic factor, which hinders the survival of a plant exposed to this factor. The presence of a lethal factor may prevent the plant from existing ab initio or may cause its death at a later stage.

*Allium cepa*: Species of the *Allium* genus, comprising bulbous plants having hollow leaves cultivated worldwide for its rounded edible bulb. Cultivar onions and shallots are *Allium cepa* species.

Recombination: Crossing-over occurring during meiosis.

The present invention provides a first type of plant, that is a plant of the *Allium cepa* or *Allium fistulosum* species which is resistant to downy mildew of onion caused by the fungus *Peronospora destructor* (Pd). According to the present invention, the resistance to downy mildew is due to a Pd resistance locus in the genome of the plant, characterized in that the resistance locus is present homozygously in the genome, that is the sequences responsible for the resistance are present in two copies in the genome of a plant according to the invention, i.e. present on both chromosomal homologues.

Indeed, the present inventors have succeeded in separating the sequences responsible for the resistance to downy mildew from the linked lethal sequences, which were identified by the inventors as being lethal if present on both chromosome homologues. By separating these two types of sequences, the inventors have thus been able to obtain a plant homozygous for the sequences of interest (Pd resistance locus), without being homozygous for the deleterious sequences (lethal factor). The invention concerns these viable plants homozygous for the sequences conferring resistance. These plants are necessarily not homozygous far the lethal sequences, which may however be present, but at only a single copy.

As these plants according to the invention are homozygous for the sequences of interest conferring resistance, any progeny of a plant of the invention will lead to a plant also resistant to downy mildew, without segregation of this feature. Indeed, any plant in the progeny will have in its genome the Pd resistance locus, which is known to be dominant over the susceptible phenotype.

A plant is considered to be resistant if it is able to restrict the growth and development of *Peronospora destructor*, by hindering the infection or combating the growth of the fungus after infection. By contrast, a plant which is unable to restrict the growth and development of *Peronospora destructor* is said to be susceptible to *Peronospora destructor*.

Said resistance according to the invention comprises resistance to natural infection by *Peronospora destructor* and also resistance to artificial inoculation by *Peronospora destructor*. Artificial tests can be carried out in greenhouses or climate rooms under more controlled environments. Both young plants and sprouting bulbs can be tested.

Protocols for testing whether a plant is resistant or susceptible to *Peronospora destructor* are reported in the article by de Vries at al (ref 3).

Resistance may also be tested genetically with molecular markers, by assaying the presence of the Pd resistance locus in the genome of a plant. The techniques which can be used are well known to the skilled man in the domain and are generally based on genic amplification.

Techniques which can be used for molecular typing include restriction fragment length polymorphism (RFLP), multilocus enzyme electrophoresis and random amplified polymorphic DNA (RAPD). Another technique which is particularly suitable for testing the presence of the Pd resistance locus in the genome of a plant, is the AFLP™ (Amplified Fragment Length Polymorphism); such a technique is described for example in Vos et al (ref 4). This technique consists in a first step of digestion of the genomic DNA with suitable restriction enzymes, simultaneously with ligation with specifically designed oligonucleotide adapters. The adapters have sequences corresponding to the restriction site, linked to an additional defined sequence. In a second step, PCR amplification of the obtained tagged restriction fragments is then carried out with primers, whose sequence comprises a sequence complementary to the adapters and 1, 2 or 3 additional nucleotides allowing discrimination between the tagged restriction fragments. This PCR amplification allows detection of restriction fragment length polymorphisms.

In example 4 below are given four specific pairs of primers which give amplified fragments of defined length, only when the Pd resistance locus is present. If a plant generates one or more of the expected amplified fragments, it can be deduced that this plant possesses the whole Pd resistance locus and is thus resistant to downy mildew. The use of molecular markers is particularly well suited in the context of the present invention.

Preferably, resistant plants according to the invention are resistant to infection by *Peronospora destructor*.

Plants according to this first type according to the invention are for example plants from the line 3591-1 which has been deposited at the NCIMB under accession number 41249. The process by which the inventors have obtained this plant is reported in example 1.

The present invention also concerns a second type of plants, which are plants possessing said Pd resistance locus heterozygously, i.e. on only one of the chromosome homologue. According to the invention, said plants can be obtained by crossing the homozygous plant mentioned above with a second plant of the *Allium cepa* or *Allium fistulosum* species, the second plant being susceptible to downy mildew of onion.

Depending on the species of the plants which are crossed, the invention thus encompasses hybrids between *Allium cepa* and *Allium fistulosum*, as well as plants of the *Allium fistulosum* species and plants of the *Allium cepa* species.

Due to the fact that the Pd resistance locus is present heterozygously in the second type of plants of the invention, the resistance trait segregates when further to self-pollinations or crossing them with other plants.

A plant according to this embodiment of the invention can be obtained by crossing a plant from the line 3591-1 which has been deposited at the NCIMB under accession number 41249, with a downy mildew-susceptible *Allium cepa* parental line. This parental line is preferably a cytoplasmic male sterile *Allium cepa* inbred line.

The second type of plant according to the invention can of course be obtained by other processes. For example, they can also be obtained by self-pollinating plants already of this type, although, as explained above, progeny of such a self-pollination is not 100% resistant to downy mildew.

According to the present invention, the Pd resistance locus is preferably present on chromosome 3, homozygously or heterozygously, in the genome of plants according to the first or second type of the present invention. Plants of the *Allium cepa* and *Allium fistulosum* species have indeed 2n=16 chromosomes which are considered to be homoeologous chromosomes (see in particular reference 8).

Plants of the invention also includes plants of the *Allium cepa* or *Allium fistulosum* species, which are resistant to downy mildew of onion caused by the fungus *Peronospora destructor* (Pd) due to a Pd resistance locus, wherein any fragment of the chromosome comprising the Pd resistance locus, can be present homozygously in progeny without causing lethality.

As mentioned above, in the proximity of the Pd resistance sequences or locus, sequences causing lethality may generally be found. The portion of the chromosome comprising the Pd resistance locus and said lethal sequences may generally not be present on both chromosome homologues, because it prevents the plant from existing. By disjoining the Pd resistance locus from the lethal sequences, the inventors have been able to obtain plants which contain the Pd resistance locus and wherein any portion of the chromosome comprising the Pd resistance locus is or may be present on both chromosome homologues, because the lethal sequences are not present.

Plants of the *Allium fistulosum* species according to the invention may be obtained by crossing a first plant of the line 3591-1 (deposited at the NCIMB under accession number 41249) with a plant of the *Allium roylei* species and then backcrossing the obtained hybrid with plants of the *Allium fistulosum* species, one or several times, that is using *Allium roylei* as a bridge species.

The invention also concerns a plant of the *Allium cepa* or *Allium fistulosum* species, which is resistant to downy mildew of onion caused by the fungus *Peronospora destructor* (Pd), wherein at least one of the homologues of chromosome 3 comprises a Pd resistance locus and any fragment of said chromosome, comprising the Pd resistance locus, can be present homozygously in progeny without causing lethality.

It must be noted that a plant being homozygous for the Pd resistance locus and heterozygous for the lethal sequences, i.e. the lethal sequences are present on only one homologue of chromosome 3, is also part of the present invention. Indeed, any fragment of at least one of the homologue of chromosome 3, the homologue comprising the Pd resistance locus without the lethal sequences, can be present homozygously in progeny without causing lethality.

Such a plant is for example plants 3591-3, 3591-4, 3591-5, 3591-6 or 3591-8 exemplified in example 3 of the experimental section of the present application.

By self-pollinating a resistant plant, it can be deduced by analysis of the progeny whether the plant corresponds to the definition given above. Example 5 gives details about the analysis to be carried out for such a determination. The main criterion to be evaluated is the percentage of progeny which is resistant. Any resistant plant is a plant according to the invention if at least 75% (+/−5% due to variability of the measures) of the progeny is also resistant. FIG. 1 exemplifies the different situations at the genomic level, leading to this percentage.

It must be noted that a plant having a Pd resistance linked to lethal sequences on only one chromosome homologue is not part of the present invention. Such a plant, after self-pollination, will give a progeny which is, according to the genetic law, 66.7% resistant, i.e. less than 75%. Such a plant can thus be discriminated from plants according to the present invention.

Such a plant is for example plant of line 2348 exemplified in example 2 of the experimental section of the present application.

Preferably, the Pd resistance locus is present homozygously in a plant according to the invention.

According to a preferred embodiment of the present invention, the Pd resistance locus, which confers resistance to infection by *Peronospora destructor*, is present on an introgression fragment; it originates from a plant which is naturally resistant to downy mildew of onion and preferably from a wild *Allium* genitor resistant, most preferably from *Allium roylei*. The presence of an introgression fragment in the genome of a plant of *Allium cepa* or *Allium fistulosum* species can be obtained by crossing said plants with an introgression partner, thus obtaining a hybrid. Said hybrid is preferably crossed back with plant of *Allium cepa* or *Allium fistulosum* species in order to minimize the introgression fragments, and then selected on the capacity to show resistance to downy mildew.

Indeed, the introgression fragments in a plant of *Allium cepa* or *Allium fistulosum* species according to the invention are preferably limited in order to have plants which share all the characteristics of interest of the parental plant but the resistance trait.

Preferably, introgression fragments in the genome of a plant according to the present invention are only present in one or both homologues of chromosome 3 and preferably in the long arm of the chromosome 3. It is preferred that the introgression fragment comprising the Pd resistance locus is less than 50% of the length of the long arm of chromosome 3, preferably less than 44%, more preferably less than 35, 30, 25 or 20% of the length of the long arm of chromosome 3. As mentioned above, the introgression fragment preferably originates from *Allium roylei* genome.

Plants according to this type are plants from the line 3591-1 which has been deposited at the NCIMB under accession number 41249.

It should be noted that one, two or more introgression fragments can be present, for example in the long arm of chromosome 3, however each fragment being distinct and disjoined from the others. There is preferably only one introgression fragment.

According to the most favourable situation, the introgression fragment present in a plant according to the invention is only the sequences strictly necessary to the resistance to downy mildew.

Plants according to the invention can be used to transfer the Pd resistance into other agronomical valuable plants, provided the plants can be crossed together. This may be done by obtaining a hybrid and then backcrossing the hybrid with the second plants, followed by self-pollinations of the obtained plants; at each step, resistant progeny is selected.

Preferably, plants according to the invention are stable for the characteristic of interest, i.e. resistance to downy mildew of onion, however not necessarily for other traits.

A plant according to the present invention may be obtained from an initial interspecific cross between a wild *Allium* genitor resistant to downy mildew of onion and *Allium cepa*. According to this situation, the introgression fragment originates from the wild *Allium* genitor.

In order to obtain a plant according to the invention, that is of the *Allium cepa* or *Allium fistulosum* species, it must be necessary to select hybrid plants resulting from the cross which share the largest phenotypic similarity with the parent of the *Allium cepa* or *Allium fistulosum* species however being resistant to downy mildew. Preferably, a plant according to the invention can be obtained after the initial interspecific cross mentioned above followed by several backcrosses with plant of the parental species and optionally one or several self-pollinations.

The steps of backcrosses and self-pollinations allow to reduce the proportion of introgression fragments in the resulting plant. The number of backcrosses which is recommended is at least 2, preferably 3, 4, 5 or 6, 7, 8 to 10 successive backcrosses may also be envisaged. The number of self-pollinations which are to be performed is between 1 and 8, preferably 2, 3, 4 or 5.

According to a preferred embodiment of the present invention, the initial interspecific cross is between wild *Allium* genitor resistant to downy mildew of onion and *Allium cepa* and the mentioned backcrosses are carried out with plants of the *Allium cepa* species.

The wild *Allium* genitor is any plant of *Allium* genus which is resistant to downy mildew of onion caused by *Peronospora destructor*, preferably a naturally resistant one, and a preferred *Allium* genitor is a plant of the *Allium roylei* species.

As mentioned above, the presence of the Pd resistance locus can be tested according to well known protocols for detecting the resistance to infections by *Peronospora destructor*. These protocols however are time-consuming. The presence of the Pd resistance locus may thus also be tested by other genetic techniques, based on genic amplification, which are well known to the skilled man in the domain.

Techniques which can be used for molecular typing include restriction fragment length polymorphism (RFLP), multilocus enzyme electrophoresis and random amplified polymorphic DNA (RAPD). Another technique which is particularly suitable for testing the presence of the Pd resistance locus in the genome of a plant, is the AFLP™ (Amplified Fragment Length Polymorphism); such a technique is described for example in reference 4. This technique is particularly suitable for the present invention.

According to the present invention, this technique called AFLP™ is used for assaying the presence of the Pd resistance locus in the genome of a plant of *Allium* genus. The restriction of the genomic DNA of the plant is preferably performed with the restriction enzymes PstI and MseI; and the ligation is performed with the following adapters:

```
alpha 5'-CTCGTAGACTGCGTACATGCA    (SEQ ID NO: 1)

CATCTGACGCATGT-5',    (SEQ ID NO: 2)
and beta 5'-GACGATGAGTCCTGAG          (SEQ ID NO: 3)

TACTCAGGACTCAT-5'.    (SEQ ID NO: 4)
```

The PCR amplification is then carried out on the restriction fragments ligated to the adapters with the following primers:

```
(A)
5'-GACTGCGTACATGCAGAAC         (SEQ ID NO: 5)
and

5'-GATGAGTCCTGAGTAACTT.        (SEQ ID NO: 6)
```

According to this procedure, the presence of a Pd resistance locus in the tested plant can be deduced from the presence of an amplified fragment of 61 nucleotides. Indeed, if such a fragment results from the preceding steps, it is indicative of the presence of a Pd resistance locus according to the invention, as can be deduced from the results reported in the example 4.

Alternatively, the method can be carried out according to the following alternative protocol:
the restriction of the genomic DNA of the plant is performed with the restriction enzymes PstI and MseI; and the ligation is performed with the following adapters:

```
alpha 5'-CTCGTAGACTGCGTACATGCA  (SEQ ID NO: 1)
              CATCTGACGCATGT-5',  (SEQ ID NO: 2)
and beta  5'-GACGATGAGTCCTGAG        (SEQ ID NO: 3)
              TACTCAGGACTCAT-5';  (SEQ ID NO: 4)
``` the PCR amplification is amplification is then carried out on the restriction fragments ligated to the adapters with the following primers:

```
(B)
5'-GACTGCGTACATGCAGAAG     (SEQ ID NO: 7)
and

5'-GATGAGTCCTGAGTAAAAC.    (SEQ ID NO: 8)
```

When such a protocol is carried out, a specific fragment of 151 nucleotides is representative of the presence of a Pd resistance locus in the genome of the tested plant, as can be deduced from the results reported in the example 4.

According to a third alternative, the method can be carried out according to the following protocol:
the restriction of the genomic DNA of the plant is performed with the restriction enzymes PstI and MseI; and the ligation is performed with the following adapters:

```
alpha 5'-CTCGTAGACTGCGTACATGCA  (SEQ ID NO: 1)
              CATCTGACGCATGT-5',  (SEQ ID NO: 2)
and beta  5'-GACGATGAGTCCTGAG        (SEQ ID NO: 3)
              TACTCAGGACTCAT-5';  (SEQ ID NO: 4)
``` the PCR amplification is amplification is then carried out on the restriction fragments ligated to the adapters with the following primers:

```
(C)
5'-GACTGCGTACATGCAGACA     (SEQ ID NO: 9)
and

5'-GATGAGTCCTGAGTAACCA.    (SEQ ID NO: 10)
```

When such a protocol is carried out, a specific fragment of 330 nucleotides is indicative of the presence of a Pd resistance locus in the genome of the tested plant, as can be deduced from the results reported in the example 4.

Example 4 of the present invention describes the use of such a method.

The present invention is also directed to a plant of the *Allium cepa* species, homozygously resistant to the downy mildew of onion, i.e. the progeny of said plant after self-pollination is 100% resistant to downy mildew, which can be obtained by carrying out the following process:

a) Interspecific cross between *Allium roylei* and *Allium cepa*;

b) Selection of an interspecific hybrid, resistant to downy mildew of onion caused by the fungus *Peronospora destructor* (Pd);

c) Backcross of said hybrid with plants of *Allium cepa*;

d) Selection of plants resistant to downy mildew of onion;

e) Self-pollination of the thus obtained plants;

f) Selection of plants homozygously resistant to downy mildew of onion.

The step a) has been proven to give viable interspecific hybrids which are male and female fertile. The interspecific cross can be made between *Allium roylei* as the male and *Allium cepa* as the female parent or on the contrary with *Allium roylei* as the female and *Allium cepa* as the male parent.

The step b) is a step of selection of plants resistant to downy mildew of onion caused by the fungus *Peronospora destructor*. As mentioned in the preceding paragraphs, the resistance may be tested by natural or artificial inoculations with known protocols described in the literature or in the experimental section of the present application. The selection may also be achieved by taking advantage of the AFLP™ method described above. Useful restriction enzymes, adapters and PCR primers are described above, along with the length of the expected amplified fragment indicative of the presence of Pd resistance locus.

According to the present invention, the plants selected at the step b) not only are resistant to downy mildew of onion, but they share also advantageously as many as possible morphological characteristics with the *Allium cepa* parent.

Step c) is concerned with backcross of the interspecific hybrid selected at step b) for its resistance to downy mildew of onion with plants of the *Allium cepa* species. These *Allium cepa* plants used for the backcross step may be from the same subspecies, variety or form than the plant used in step a) as parent for the interspecific hybrid, but not necessarily.

After plants resulting from the backcross are obtained, plants are selected which are resistant to downy mildew of onion. As mentioned for step b), this selection may be achieved by testing the capacity to resist an infection by *Peronospora destructor*, or by achieving molecular typing, for example by the AFLP™ technique.

In a preferred embodiment of the present invention, this step c) followed by step d) are advantageously repeated at least once, that is there are at least two successive backcrosses. The number of backcrosses may vary between 2 to 10, preferably 3, 4, 5 or 6, The step e) is a step of self-pollination or selfing, which is well known by one skilled in the art.

This step of self-pollination is followed by selection of plants resistant to downy mildew of onion, which share all the traits characteristic of a plant of the *Allium cepa* species.

Preferably, these steps of self-pollination and selection are repeated at least once, i.e. at lest two series of self-pollination and selection are achieved. These steps are preferably carried out 2, 3, 4, 5 or 8 times, i.e. they are repeated 1, 2, 3, 4 or 7 times.

The last step of the process concerns the selection of a plant which is homozygously resistant to downy mildew of onion caused by *Peronospora destructor*. This homozygosity may be tested by achieving step e) and checking that 100% of the progeny is resistant to downy mildew.

According to the present invention, this last step of selection may be achieved preferably by using a molecular typing technique, for example the AFLP™ technique as described in the preceding sections and preferably with the restriction enzymes, adapters and primers recited before.

The present invention also concerns a method for the production of a plant of the *Allium cepa* species which is resistant to downy mildew of onion caused by the fungus *Peronospora destructor* (Pd) which comprises the following steps:

a) Obtaining an *Allium roylei* resistant to downy mildew of onion;

b) Making a interspecific cross between said *Allium roylei* and an *Allium cepa*;

c) Selecting an interspecific hybrid resistant to downy mildew of onion;

d) Backcrossing said hybrid with plant of *Allium cepa*;

e) Selecting plants resistant to downy mildew of onion;

f) Self-pollinating the resistant plant obtained at step e);

g) Selecting plants homozygously resistant to downy mildew of onion.

According to the present invention molecular markers are used in steps c), e) and/or g) for selecting plants resistant to downy mildew of onion.

The different steps of the method are as explained in the preceding paragraphs. The preferred embodiments of the process were also mentioned previously, in particular, the repetition of the steps d) and e) and of the steps f) and g). The steps of selection may also be achieved as explained previously. They are preferably achieved using a molecular typing method making use of molecular markers. A particularly preferred method is AFLP™ which is described in the preceding sections. According to the invention, molecular markers may be used in the selection step c) only, or in the step e) only, or in step g) only, or in each of these steps, or in two of three.

At each selection step, the selected plants are preferably plants sharing the highest number of traits characteristic for *Allium cepa*. According to this procedure, the introgression fragments originating from the first *Allium roylei* genitor are minimized at each step. The traits characteristic for *Allium cepa* are as disclosed in the Guidelines for the Conducts of Tests for Distinctness, Uniformity and Stability (reference TG/46/6), in connection with the treaty UPOV.

According to the invention, the method may also comprise an additional step of crossing the plant obtained at the end of step g) with a plant of *Allium cepa* species which is susceptible to downy mildew of onion. The resulting plant is resistant to downy mildew, as the plant obtained at the end of step g) is homozygously resistant to downy mildew.

As already mentioned, the selection step c), e) and/or g) may be carried out using the AFLP™ technique. As exemplified in the present application, the restriction enzymes used in this technique are preferably enzymes PstI and MseI. Suitable pair of adapters for the ligation step is:

```
alpha 5'-CTCGTAGACTGCGTACATGCA    (SEQ ID NO: 1)
              CATCTGACGCATGT-5',  (SEQ ID NO: 2)
and beta  5'-GACGATGAGTCCTGAG         (SEQ ID NO: 3)
                 TACTCAGGACTCAT-5'.  (SEQ ID NO: 4)
```

For the PCR amplification step, suitable pairs of primers which can be used are:

```
(A)
5'-GACTGCGTACATGCAGAAC    (SEQ ID NO: 5)
and

5'-GATGAGTCCTGAGTAACTT;   (SEQ ID NO: 6)

(B)
5'-GACTGCGTACATGCAGAAG    (SEQ ID NO: 7)
and
```

```
-continued
5'-GATGAGTCCTGAGTAAAAC;   (SEQ ID NO: 8)
and (C)
5'-GACTGCGTACATGCAGACA    (SEQ ID NO: 9)
and

5'-GATGAGTCCTGAGTAACCA.   (SEQ ID NO: 10)
```

Several fragments are amplified and can be detected on an agar gel after this PCR amplification. However, the presence of a fragment having 61 nucleotides when the pair of primers (A) is used, is indicative of the presence of a Pd resistance locus in the genome of the tested plant. Alternatively, when the pair of primers (B) is used, the length of the indicative amplified fragment is 151 nucleotides, and 330 when the pair of primers (C) is used.

In a preferred embodiment of the invention, when using the AFLP™ technique, additional PCR amplifications may also be carried out, in order to detect false positives. According to this procedure, amplifications are carried out with at least one pair of primers chosen amongst the following pairs of primers:

```
(A')
5'-GACTGCGTACATGCAGAAG    (SEQ ID NO: 7)
and

5'-GATGAGTCCTGAGTAAAAC;   (SEQ ID NO: 8)

(B')
5'-GACTGCGTACATGCAGAAC    (SEQ ID NO: 5)
and

5'-GATGAGTCCTGAGTAACTT;   (SEQ ID NO: 6)

(C')
5'-GACTGCGTACATGCAGAAA    (SEQ ID NO: 11)
and

5'-GATGAGTCCTGAGTAACAC.   (SEQ ID NO: 12)
```

The amplified fragments resulting from these additional amplifications are used as negative controls. No fragment of the length expected when using pair of primers (A), (B) or (C) must be detected when using pair of primers (A'), (B') or (C').

The present invention also encompasses plants of the *Allium* genus which can be obtained by the methods as described, in particular by the method according to the preferred embodiments.

The invention also concerns a hybrid *Allium cepa* plant obtainable by crossing a downy mildew-susceptible *Allium cepa* parental line with a plant homozygously resistant to downy mildew of onion according to the invention. Said plant is for example obtainable by carrying out the method of the invention as disclosed above.

The *Allium cepa* parental line may be any line of the species *Allium cepa*, it is preferably a line well described and known for characteristics of interest. For example it is a cultivar line known for its taste, fast growing or other agronomical important traits.

According to a preferred embodiment, the parental line is a cytoplasmic male sterile *Allium cepa* inbred line.

Any plant of the invention which has been described is, according to a preferred embodiment of the invention, a cultivated onion or shallot.

EXAMPLES

Example 1

Figure 1:
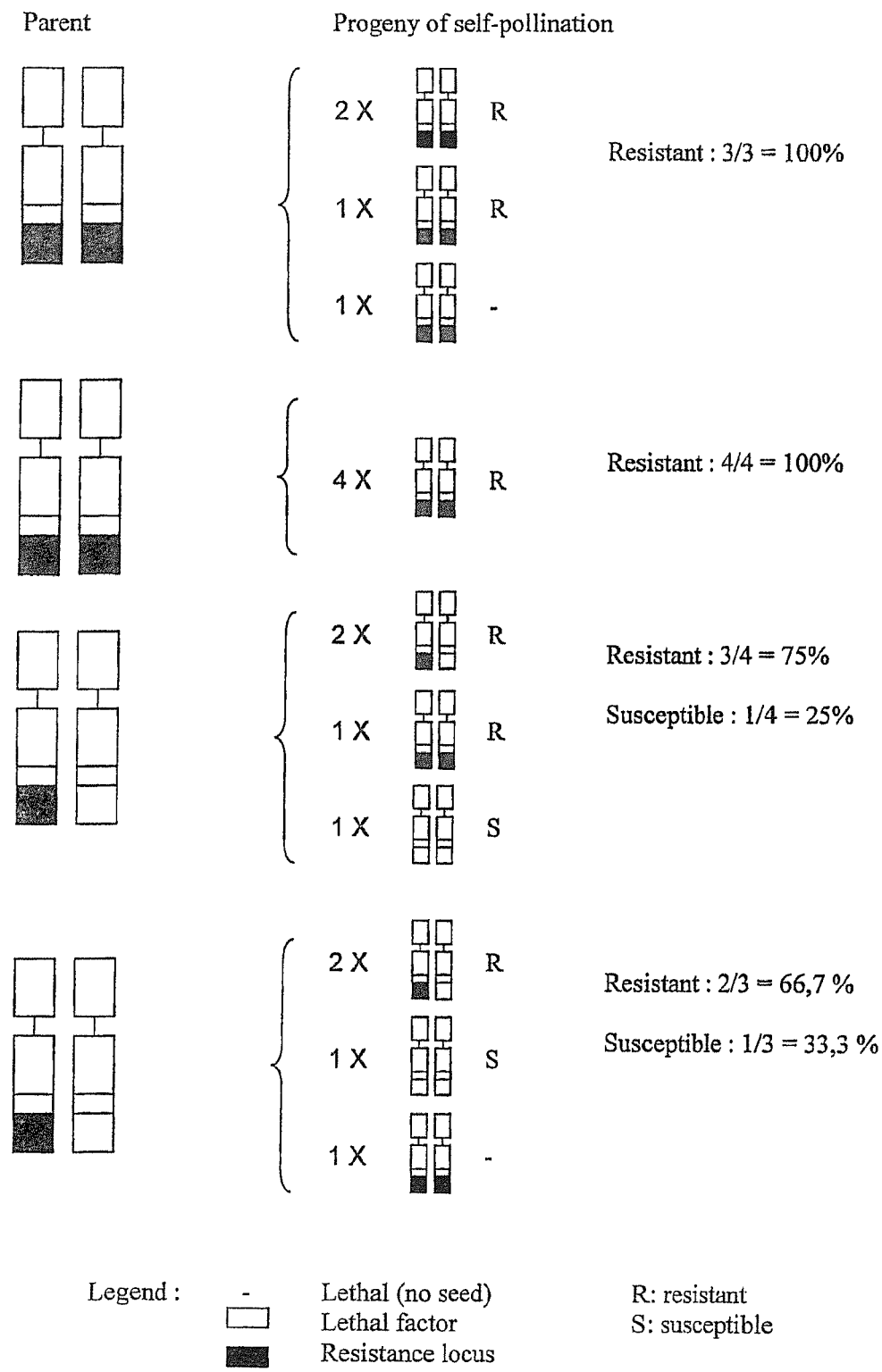
FIG. 1: This figure illustrates schematically a potential way of transmission of Pd resistance locus and lethal sequences to the progeny of self-pollination for 4 different resistant *Allium*. The right column gives the percentage of resistance in progeny and is indicative of whether the parent plant has at least a homologue of chromosome 3 which bears the resistance locus without the lethal sequences.

Obtaining of a Homozygously Resistant Line of *Allium cepa*

Introduction:

Downy mildew in onion is caused by the fungus *Peronospora destructor* (Berk.) Casp. (Mukerji, ref 5). It is an obligate pathogen that can only be maintained on plant tissue, not on agar or liquid media in vitro.

Tests on disease resistance can be carried out in various ways, see for example de Vries et al (ref 3). Spontaneous epidemics may occur in the field, if conditions are favourable for the disease. Artificial tests can be carried out in greenhouses or climate rooms under more controlled environments. Both young plants and sprouting bulbs can be tested. The symptoms are yellowing of the leaves and grey sporulation.

In the breeding program followed by the inventors, various methods have been applied during the process of backcrossing and during the process of selfing in order to obtain homozygous lines.

This report describes the trials which resulted in the conclusion that the resistance did not inherit as simply as expected: monogenic dominant, and which resulted in the production of the line 3591 of the invention, with complete resistance to downy mildew.

Materials and Methods.

The starting point of this study is the plant called $F_1BC_2$ disclosed in de Vries et al (ref 3). This plant has been obtained by a first interspecific cross between *Allium cepa* and *Allium roylei* (F1), followed by two successive backcrosses to *Allium cepa* (BC2). The present inventors have continued to carry out backcrosses of said plant material to their breeding lines and they have carried out selfings of the BC5 generation in order to obtain homozygous lines. S1, S2 and S3 indicates respectively that 1, 2 or 3 successive selfing (self-pollination) steps have been carried out.

A first field test was carried out with F3 lines ($F_1BC_5S_2$), derived from selfing resistant plants of different F2 populations ($F_1BC_5S_1$). Plants were sown out on the main breeding field of the inventors.

Spreader bulbs that were previously inoculated in the greenhouse were placed in the field (Hildebrand et al, ref 7). Inoculum was made by suspending conidiospores in demi-water. Leaves with spores were washed off with demi-water over two layers of cheese cloth. The suspension was diluted to $5.0 \times 10^4$ spores/ml. The spores were inoculated into bulbs, from the bulb equator to the basal plate, with a syringe with needle. The bulbs were placed in plastic bags with some humid paper during 24 h at 10° C. After that the temperature was raised to 15° C. in order to stimulate the growth of mycelium. Then the bulbs were planted out in the field.

An epidemic started and during the second half of August infected plants were counted. During the growing season and until the stage of fall over of the leaves and ripening of the bulbs, counts were made of non-infected bulbs in order to estimate the resistance score and segregation ratio of the different lines. Resistant plants do not show symptoms at all. If any lesions could be scored, the plant was considered as susceptible.

In second field test, 353 plots were drilled on the breeding field, in the first week of April. The field was surrounded by bulbs, in order to stimulate the development of the downy mildew epidemic. A heavy infection started which resulted in a 100% infection of control plots of the susceptible variety Staccato. Counts were made of infected and non-infected plants. Bulbs of relevant lines were harvested and used for further research and seed production for the year after.

Results.

The first field test resulted in heavy infection of the onion plants. As long as the symptoms could be scored reliably, counts were made of the susceptible plants. Some early lines fell over in an early stage and no distinction could be made between dying of the leaves and downy mildew symptoms. For these lines only the susceptible plants were scored and not the resistant ones, because the resistant class would in these early lines contain many escapes. In total there were 20 lines. 34 lines were counted for both susceptible and resistant plants and these lines were falling over much later and the scoring on resistance could be done reliably. Data are given in table 1.

The second field test again gave a high downy mildew infection. Special control plots of the susceptible variety Staccato were 100% infected. In this field test of 353 different breeding lines, only one number was found that gave no infected plants. This breeding line 4018282 sown under the plot number 3591 gave 140 plants not infected. 21 other F4 lines ($F_1BC_5S_3$), derived by selfing from the same F3 line, 3997284, showed segregation for resistance, table 2.

TABLE 1

Downy mildew field test n° 1:

| Breeding line F3 S2 | Percentage Resistance | Plants susceptible | Plants resistant |
|---|---|---|---|
| 3977304 | 72.6 | 63 | 167 |
| 3977305 | 67.5 | 124 | 258 |
| 3977307 | 90.7 | 26 | 254 |
| 3977311 | 52.9 | 177 | 199 |
| 3977313 | 57.7 | 224 | 305 |
| 3977319 | 55.6 | 248 | 311 |
| 3977322 | 51.7 | 357 | 382 |
| 3977326 | 50.9 | 82 | 85 |
| 3977328 | 59.1 | 56 | 81 |
| 3977333 | 57.1 | 275 | 366 |

TABLE 1-continued

Downy mildew field test n° 1:

| Breeding line F3 S2 | Percentage Resistance | Plants susceptible | Plants resistant |
|---|---|---|---|
| 3977334 | 62.5 | 48 | 80 |
| 3977336 | 66.7 | 25 | 50 |
| 3977337 | 56.2 | 312 | 401 |
| 3977338 | 70.3 | 33 | 78 |
| 3977343 | 74.0 | 20 | 57 |
| 3977344 | 68.4 | 24 | 52 |
| 3977350 | 58.3 | 43 | 60 |
| 3977351 | 53.1 | 38 | 43 |
| 3977357 | 73.2 | 56 | 153 |
| 3977358 | 92.5 | 7 | 86 |
| 3977367 | 68.3 | 33 | 71 |
| 3977375 | 60.9 | 88 | 137 |
| 3977377 | 71.0 | 54 | 132 |
| 3977378 | 57.4 | 103 | 139 |
| 3977379 | 56.0 | 80 | 102 |
| 3977380 | 61.7 | 75 | 121 |
| 3977381 | 66.5 | 56 | 111 |
| 3977382 | 58.9 | 304 | 436 |
| 3977385 | 66.3 | 31 | 61 |
| 3977387 | 60.2 | 37 | 56 |
| 3977392 | 55.9 | 152 | 193 |
| 3977394 | 72.1 | 39 | 101 |
| 3977395 | 55.0 | 45 | 55 |
| 3977396 | 47.6 | 66 | 60 |
| Total | 60.7 | 3401 | 5243 |

TABLE 2

Downy mildew field test n° 2:

| Breeding line F4 S3 | Percentage Resistance | Plants susceptible | Plants resistant |
|---|---|---|---|
| 4018268 | 58.3 | 63 | 88 |
| 4018269 | 61.5 | 82 | 131 |
| 4018270 | 69.2 | 66 | 148 |
| 4018272 | 61.7 | 57 | 92 |
| 4018273 | 64.5 | 60 | 109 |
| 4018274 | 75.1 | 46 | 139 |
| 4018275 | 71 | 67 | 164 |
| 4018276 | 68.5 | 78 | 170 |
| 4018278 | 63.7 | 85 | 149 |
| 4018279 | 56.9 | 97 | 128 |
| 4018280 | 66.9 | 46 | 93 |
| 4018281 | 60.5 | 90 | 138 |
| 4018282 | 100 | 0 | 140 |
| 4018283 | 62.2 | 56 | 92 |
| 4018284 | 66.7 | 47 | 94 |
| 4018287 | 54.8 | 84 | 102 |
| 4018288 | 71.4 | 46 | 115 |
| 4018289 | 71.5 | 55 | 138 |
| 4018290 | 53.8 | 55 | 64 |
| 4018291 | 67.8 | 38 | 80 |
| 4018292 | 65.2 | 64 | 120 |
| 4018293 | 72.2 | 80 | 208 |

Discussion.

The field trial n° 1 gave the first clear indication that breeding for downy mildew resistant onions was not as simple as previously expected. In case of a monogenic, dominantly inherited resistance, one would normally expect to find at least 1/3 of the lines being fully resistant, after setting resistant F2-plants. Only RR plants give a fully resistant progeny, Rr plants will segregate, and in a F2 after selection for resistance RR plants comprise 1/3 of the population (where "R" stands for allele bearing the dominant resistance gene, "r" for the recessive susceptible gene).

54 lines were tested and 34 could reliably be scored for both resistance and susceptibility, but all of the 54 lines segregated. This means a ratio significantly different from 1/3.

Total ratio of resistant plants over all lines was lower than expected (60, 65%) If a heterozygous plant was selfed, a resistant ratio of 75% was expected in case of a single dominant gene.

Individual lines, like 3977307 and 3977358 gave a different ratio. This may be caused by escapes. Inbred lines derived from 3977303 have been tested, and all segregated, with ratios varying between 52% and 73% (data not shown). Plants that failed to be infected are classified as resistant, but escaped to show symptoms, maybe due to early decay of foliage, low population, that leads to a less humid micro-climate or other disease or trips infections.

The field test n° 2 resulted in the discovery of the 3591-plot, containing line 4018282. This line did not show susceptible plants in a heavy infected field. The field contained 353 lines which confirmed the complexity of the inheritance. Otherwise a much higher frequency of homozygous lines was found and not only line 4018282/3591.

Out of plot 3591 plants were taken into the greenhouse for research on the *A. roylei*-introgression fragment to be carried out (see example 3) and for seed production purposes. The results presented in example 3 showed that 3591 contained a smaller introgression fragment. Some of the plants are heterozygous for the small and large introgression fragments and plant 3591-1 was homozygous for the small introgression fragment.

The uniqueness of this line is illustrated by the results of the sister lines given in table 2. These lines have all been derived from the same F3 line by selfing and none of them show homozygosity.

Example 2

Genomic In Situ Hybridization (GISH) with the Breeding Line 2348, Generation $F_1BC_5S_3$ (Breeding Line 2348 from Sample Number 4008191 of Plot 2348 Gave a 66% Resistance in the Field)

The technique of Genomic in situ Hybridization (GISH) has been developed in onion by Khrustaleva and Kik (ref 9 and 10) and has been used in the present invention in order to distinguish the genomic *Allium roylei* inserts I segments from the *Allium cepa* chromosomes. This technique thus allows the visualization of the introgression fragments from *Allium roylei* in the genome of an *Allium cepa* plant.

A first set of experiments were carried out by Plant Research International BV, Wageningen (NL), on resistant plants, however segregating, onion plants, which correspond to 14 plants $F_1BC_5S_3$, wherein $F_1$ is the interspecific hybrid between *Allium roylei* and *Allium cepa*, $BC_5$ indicates 5 successive backcrosses and $S_3$ 3 successive self-pollinations.

Introduction:

GISH is a powerful technique for detection of the introgression of chromatin material from one species onto another species. The advantage of GISH is that the introgression process is visualized by means of 'pictures of the introgressed genome'. With this technique, it is also possible to establish if a particular region of the genome is homozygous or heterozygous, thanks to the use of molecular cytogenetic markers which are co-dominant. By this technique, it is also possible to determine in which chromosome an introgressed gene of interest is present.

Plant Material:

The starting material is the breeding line 2348, generation $F_1BC_5S_3$. Young root tips are collected and up to 100 slides are made for metaphase spread analysis (for method description, see Khrustaleva and Kik, (ref 9 and 10)). The slides with well spread metaphases and which contain a full set of chromosomes (2n=2x=16) are selected for GISH experiments.

Method:

Genomic DNA is extracted from young leaves of *A. cepa* and *A. roylei* using the CTAB method of Rogers and Bendich (ref 13).

Genomic DNA of *A. roylei* is labeled with Dig-11-dUTP (Digoxigenin-11-2'-deoxy-uridine-5'-triphosphate) by a standard nick-translation protocol (Boehringer, Manheim, Germany).

Genomic DNA of *A. cepa* is used as a block DNA. In situ hybridization, immunological detection and microscopy procedure are as previously described by Khrustaleva and Kik, (ref 9 and 10). Karyotype analyses are carried out according to the standard onion nomenclature system proposed by Kalkman (ref 12) and confirmed by the Fourth Eucarpia *Allium* Symposium by de Vries (ref 8). The chromosome measurements from 3-5 metaphases per each accession are performed with a free software programme for Windows from Colorado State University: (www.colostate.edu/Depts/biolog/MicroMeasure).

Figure 2A:
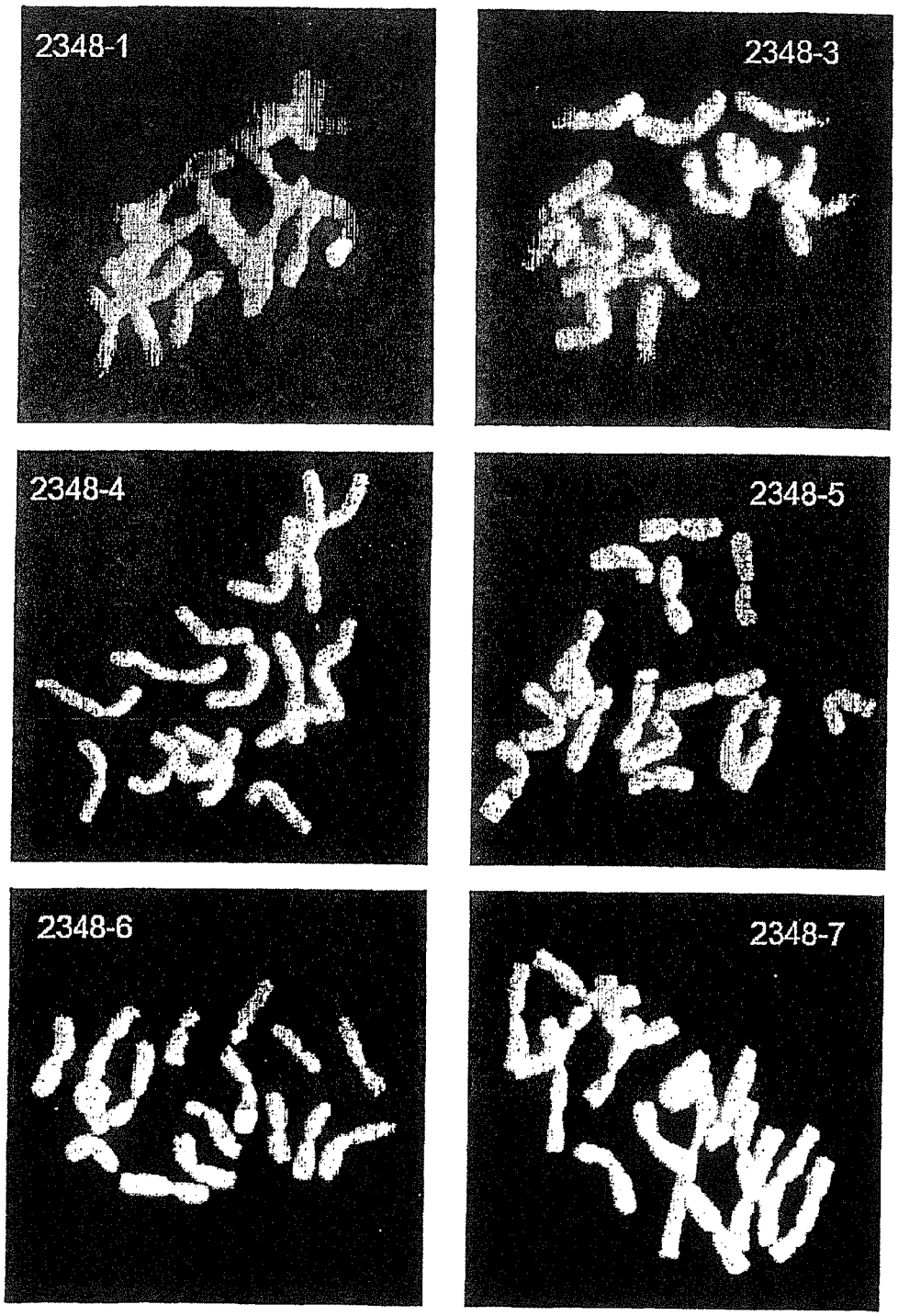
FIG. 2: this figure depicts the GISH karyotypes for the 14 downy mildew resistant plants from population 2348, which have been analysed according to the protocol described in example 2. 2348-1, 2348-3, 2348-4, 2348-5, 2348-6, 2348-7, 2348-8, 2348-11, 2348-13, 2348-14, 2348-15, 2348-16, 2348-18, and 2348-19 are different plants from the same parental line 2348.
Figure 2B:
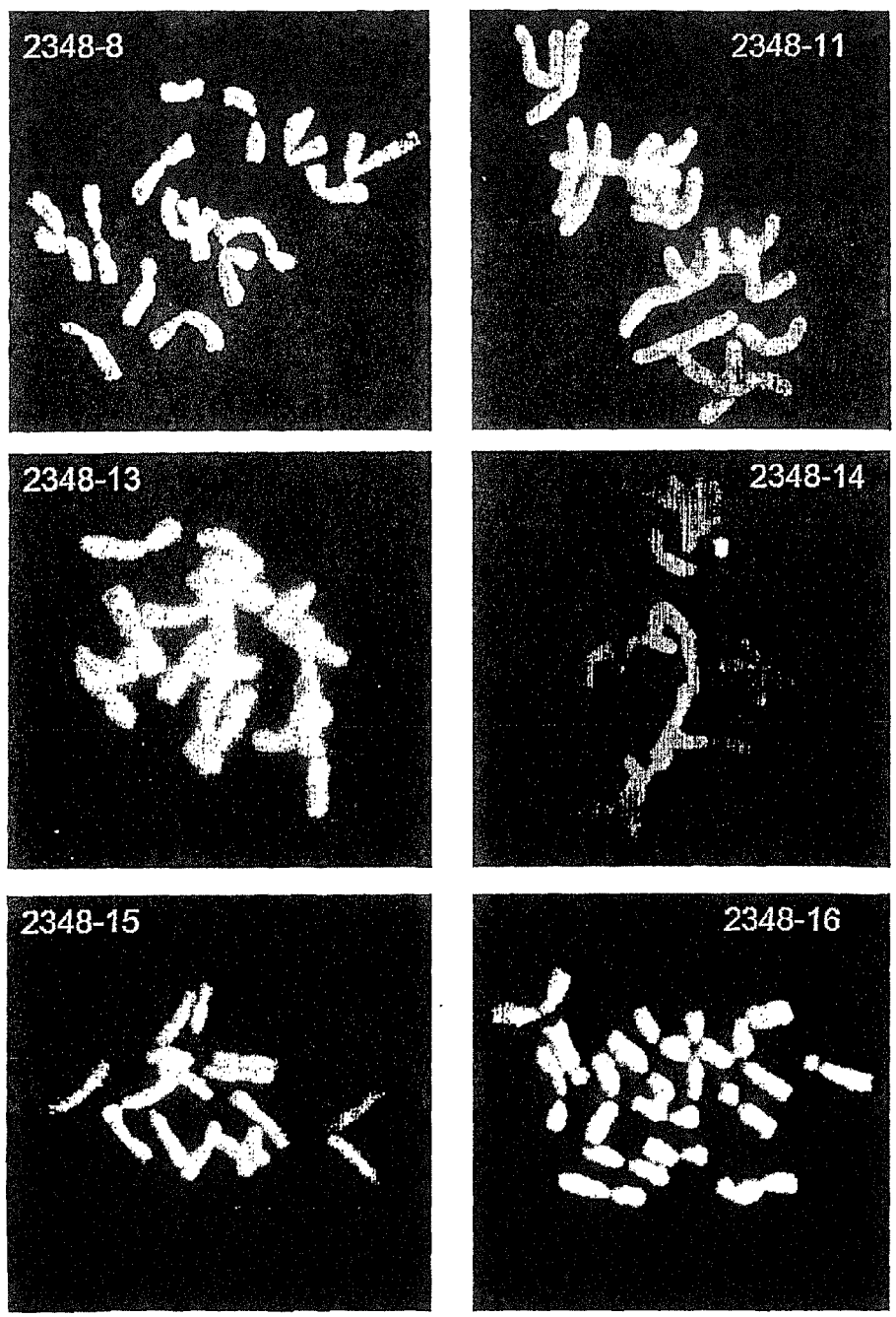
Figure 2C:
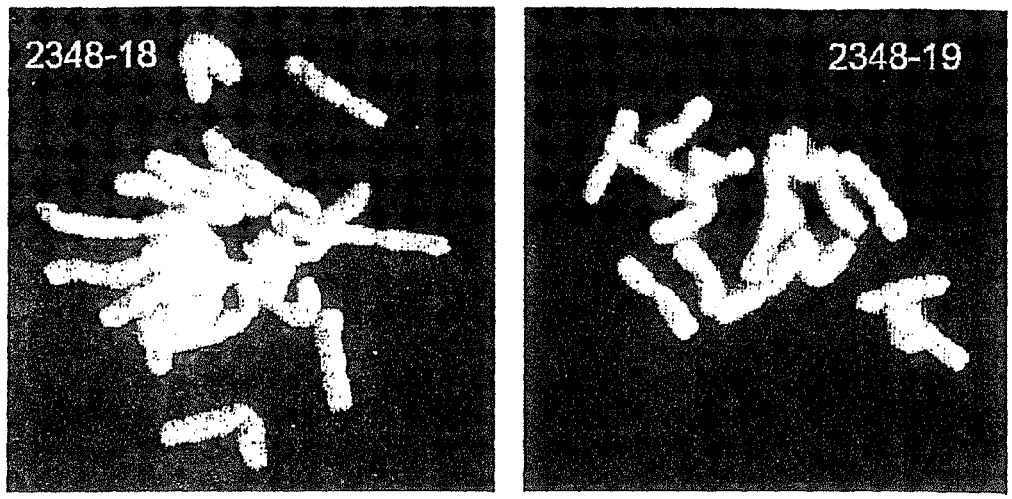

Results:

GISH analysis of 14 resistant plants from the breeding line 2348, generation $F_1BC_5S_3$ showed that all plants possess the *A. roylei* segment harbouring the gene(s) for downy mildew resistance (FIGS. 2A, 2B and 2C). Karyotype analysis revealed that the recombinant chromosome which carried the *A. roylei* segment is chromosome 3 (centromere index: 41.7; relative chromosome length: 13.8). Thirteen plants did possess only one *A. roylei* segment on chromosome 3, the other homologous chromosomes proved to be composed of only *A. cepa* chromatin. Without any doubt, these results proved that all 13 plants of breeding line 2348 are heterozygous for the segment containing the downy mildew resistance gene(s). Accession 2348-5 possesses two *A. roylei* segments: one on the long arm of chromosome 3 that carried the downy mildew resistance gene(s) and an additional one on the long arm of chromosome 4 (centromeric index: 39.3; relative chromosome length: 12.6). Both segments are heterozygously present in the genome.

GISH analysis allows also the size determination of the introgressed segment on the long arm of chromosome 3 from *A. roylei* into the *A. cepa* chromosome. The segment on average is 25.2% of the entire chromosome length and 43.9% of the long arm length.

Discussion:

By this method, the introgression of *A. roylei* chromatin material carrying downy mildew resistance genes into onion genome has been successfully detected. The present data proves the heterozygous nature of the downy mildew resistance gene(s) in breeding line 2348, generation $F_1BC_5S_3$. In all 14 individuals selected as resistant in the field, was found an *A. roylei* segment in only one homologue of chromosome 3. The aforementioned results could be explained by hypothesizing that a gene (or lethality factor) which is necessary for the *A. cepa* development, for example for seed development, and located near the downy mildew resistance gene(s), is responsible for the absence of homozygous plants. Indeed, it may be supposed that the replacement of an essential *A. cepa* gene by the corresponding *A. roylei* gene during introgression leads to a severe disturbance of the plant development, for example seed development, when placed in an *A. cepa* cytoplasm background. A viable homozygous resistant onion can be obtained only if recombination occurs between the downy mildew resistance gene(s) and the lethality factor, should this be possible.

During backcrossing to *A. cepa* and selection for downy mildew resistance, only those plants containing the *A. roylei* segment harbouring the downy mildew resistance gene(s) will be maintained. This leads eventually to plants, which consist only of *A. cepa* chromatin and a segment of *A. roylei*. However, according the above-mentioned hypothesis, this segment has replaced the *A. cepa* gene necessary for development. In a heterozygous condition, seeds develop and plants will be obtained, but in homozygous condition no plants are formed.

Example 3

Genomic In Situ Hybridization with the Breeding Line 3591, Generation $F_1BC_5S_3$ Introduction:

Following the analysis of 14 downy mildew resistant plants from breeding line 2348, generation $F_1BC_5S_3$, it was shown that all plants were heterozygous for the Pd resistance locus. The *A. roylei* segment harbouring the gene(s) for downy mildew resistance was detected only on one of the homologues of chromosome 3, the other homologue consisting entirely of *A. cepa* chromatin. This further analysis concerns the breeding line 3591 in which no segregation takes place for downy mildew resistance in the fields. In view of this, it is expected to find in this population, via GISH, plants which are homozygous for the area of chromosome 3 which harbours the downy mildew resistance locus.

Plant Material:

From 6 individual plants, breeding line 3591, generation $F_1BC_5S_3$, young root tips are collected and up to 50 slides are made for metaphase spread analysis (for method description, see Khrustaleva and Kik, ref 9). The slides with well spread metaphases and which contain a full set of chromosomes (2n=2x=16) are selected for GISH experiments.

Methods:

Details are given under section "method" of the previous example.

Figure 3:
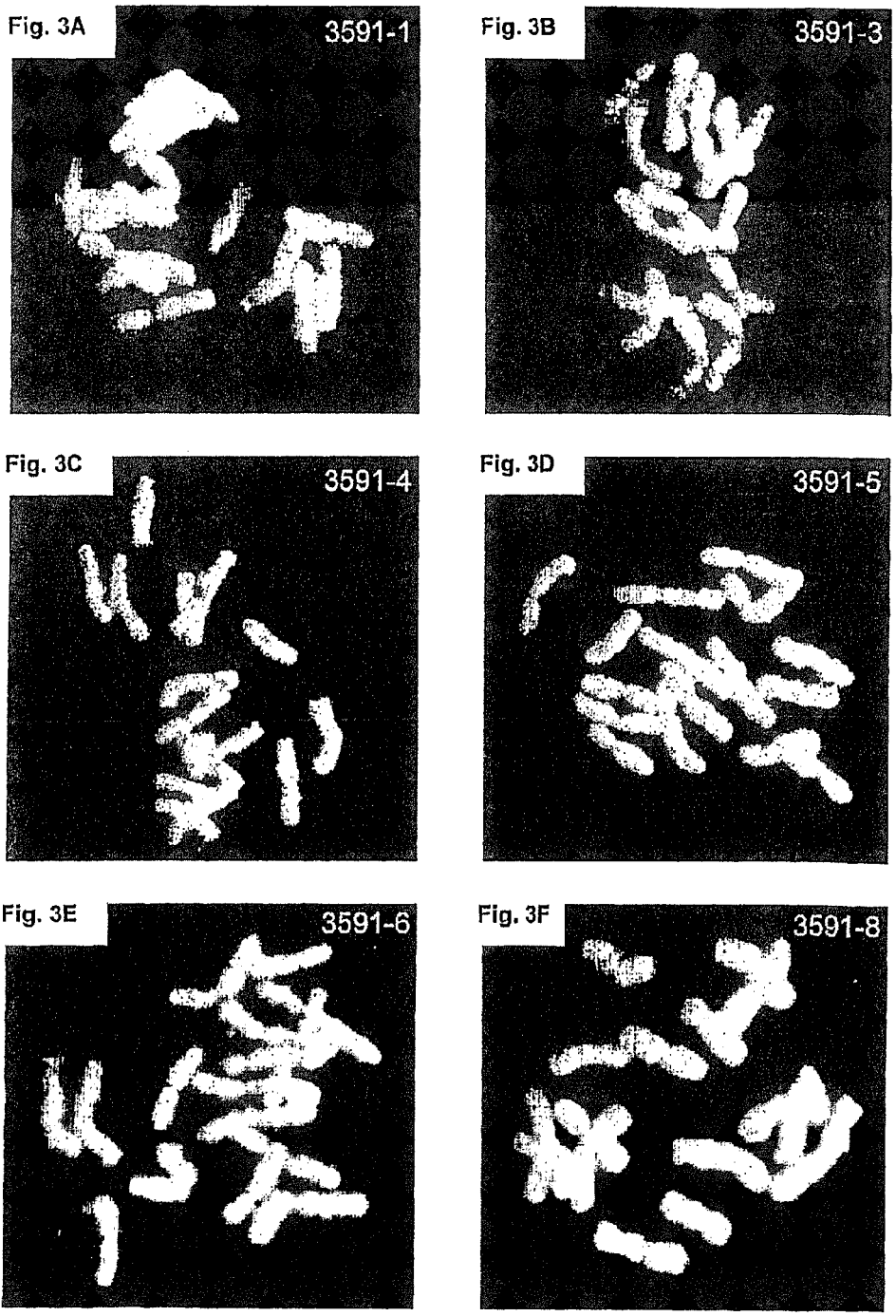
FIG. 3: this figure depicts the GISH karyotypes for the 6 downy mildew resistant plants from population 3591, which have been analysed according to the protocol described in example 2. 3591-1 (FIG. 3A), 3591-3 (FIG. 3B), 3591-4 (FIG. 3C), 3591-5 (FIG. 3D), 3591-6 (FIG. 3E) and 3591-8 (FIG. 3F) are different plants from the same parental line 3591.

Results:

Plant Research International BV, Wageningen, NL carried out GISH analyses of 6 resistant plants from the breeding line 3591, generation $F_1BC_5S_3$ which showed that all plants are homozygous *A. roylei* for the area harboring the downy mildew resistance locus (see FIGS. 3A to 3F). Karyotype analysis reveals the presence of an *A. roylei* segment in both homologues of chromosome 3 (centromere index: 41.7; relative chromosome length: 13.8). Amongst 6 analyzed plants, accession 3591-1 possesses 2 small segments on both homologues of chromosome 3 (FIG. 3A). The size of the *A. roylei* introgressed segments is the same on both homologues and averages: 17.9±0.78% of the length of the long arm. Five plants, namely accession number 3591-3, 3591-4, 3591-5, 3591-6 and 3591-8, possess two *A. roylei* introgressed segments that differed in size. (FIGS. 3B, 3C, 3D, 3E and 3F) The size of the larger segment averages 42.8±1.09% of the length of the long arm and the size of smaller one averages 17.9±0.78%.

Discussion:

The present results confirm the hypothesis put forward to explain the heterozygous nature of the downy mildew resistance locus in breeding line 2348. It might be indeed hypothesized that a lethality factor, deleterious for plant development and which is located near the downy mildew resistance gene(s), is responsible for the absence of homozygous resistant plants, or hypothesized that an essential *A. cepa* gene, necessary for plant development, is knocked out by the introgression and is responsible for the absence of homozygous resistant plants.

It is supposed that the *A. roylei* introgression segment possesses also the corresponding gene that does not function in an exclusive *A. cepa* cytoplasm (i.e. nucleo-cytoplasmic interaction). In a homozygous *A. roylei* condition, the essential *A. cepa* gene will be fully replaced by the corresponding *A. roylei* gene, consequently it will give no viable seeds. Only if recombination occurs between the downy mildew resistance gene(s) and the essential gene (or lethality factor), a viable homozygous resistant plant will be obtained. GISH analysis of breeding line 3591 proves that a homozygous resistant plant (3591-1) can be obtained due to a recombination event between the resistance gene and the lethality factor. The five other accessions possess both small and large *A. roylei* introgression segments, which means that these plants are homozygous for the resistance gene(s) and heterozygous for the *A. roylei* lethality factor.

It must be noted that, as expected from the hypothesis mentioned above, no plants possessing two large *A. roylei* introgression segments have been found, because this genetic constitution results in no seed development.

Example 4

Identification of Markers Linked to the *Peronospora destructor* Resistance Locus (Derived Form *A. roylei*)

Plant material (number of individuals):
1× *Allium roylei* (homozygous resistant)
4× (named AcA to AcD) and 24× (named Ac01 to Ac24) *Allium cepa* (homozygous susceptible)
1×3591-1 (homozygous resistant; small introgression fragments)
1×3591-3 (homozygous resistant, small and large introgression fragments)
14×2348-* (heterozygous resistant; large fragment).

Introduction:
For complement information on the AFLP™ technique, reference is made to the publication referenced under n° 4.

The aim of this example is to identify AFLP™ markers linked to the *Peronospora destructor* resistance locus in onion. The resistance locus is derived from *Allium roylei*.

As shown in example 2, a large introgression fragment has been identified in some individuals (individuals 2348-*). Besides these individuals, also two individuals were obtained which possess a smaller introgression fragment (3591-1; small fragment, and 3591-3; small and large fragments). To identify markers associated with the resistance locus, and especially obtain markers which are located on the smaller introgression fragment, an adapted Bulked Segregant Analysis (BSA, see Michelmore, ref 11) strategy was carried out on four individuals/pools:

I: individual 2348-6; heterozygous resistant; large introgression fragment,
II: individual 3591-1; homozygous resistant; small introgression fragment,
III: individual *Allium roylei*; homozygous resistant,
IV: a pool of four *A. cepa* individuals (AcA to AcD); homozygous susceptible.

The four separate *Allium cepa* individuals, 13 remaining '2348' individuals and individual 3591-3 were used for verification of the linked markers. Markers which were found to be linked to the trait of interest are finally checked on a set of 24 *Allium cepa* individuals (Ac01 to Ac24) to identify false positive markers.

Results:
Biological material: DNA was extracted from leaf material of 31 individuals (28× *Allium cepa* and individuals 3591-1, 3591-3 and *Allium roylei*) and DNA of the 14× '2348' individuals and for all individuals PstI/MseI templates were generated. No reliable AFLP™ fingerprints could be generated for the individuals 2348-4, 2348-5, 2348-11 and 3591-3, therefore these individuals were excluded from further analysis.

Marker identification and verification:
An adapted BSA approach was carried out on four individuals or pool I, II, III, IV as described above.

The BSA was carried out using 96 primer combinations in the PstI+3/MseI+3 matrix, an overview of the primer combinations used is given in table 3 and table 6 gives the nomenclature of AFLP™ primer enzyme combinations.

The BSA resulted in the identifications of 34 candidate markers of which eight candidate markers are possibly linked to the small introgression fragment. From these 34 candidate markers, a selection was made of 13 markers including the eight markers that are possibly linked to the small introgression fragment. This selection of 13 markers was used for verification on more individuals. For the verification four *Allium cepa* individuals, the 13 remaining '2348' individuals and individual 3591-3 were used.

TABLE 3

Primer combination used for the BSA approach.

| | M32 | M34 | M35 | M37 | M47 | M48 | M50 | M51 | M54 | M59 | M60 | M62 |
|---|---|---|---|---|---|---|---|---|---|---|---|---|
| P31 | X | X | X | X | X | X | X | X | X | X | X | X |
| P32 | | | | | X | X | X | X | X | X | X | X |
| P33 | X | X | X | X | | | | | | | | |
| P38 | | | | | X | X | X | X | X | X | X | X |
| P39 | X | X | X | X | X | X | X | X | X | X | X | X |
| P35 | X | X | X | X | X | X | X | X | X | X | X | X |
| P42 | | | | | X | X | X | X | X | X | X | X |
| P43 | X | X | X | X | X | X | X | X | X | X | X | X |
| P44 | | | | | X | X | X | X | X | X | X | X |
| P45 | X | X | X | X | X | X | X | X | X | X | X | X |

On basis of the verification, three candidate markers (of which two are possibly linked to the small introgression fragment) did not show a clear linkage with the trait of interest. However a total of four respectively six candidate markers, showed a clear linkage with the large respectively small introgression fragment. However two of these candidate markers, linked to the small introgression fragment are also present in one of the four *Allium cepa* individuals. Therefore these markers are found to be not useful for further analysis. The results of the verification are shown in Table 4.

Markers P32/M62-061, P33/M32-151, P35/M51-330 and P43/M35-190 are found to be linked to the small introgression fragment.

Extra-verification on 24 *Allium cepa* individuals:

To overcome false positive markers the four candidate markers (P32/M62-061, P33/M32-151, P35/M51-330 and P43/M35-190) linked to the small introgression fragment were checked on 24 extra *Allium cepa* individuals (Ac01 to Ac24). The obtained marker scores are in accordance with the expected score (see table 5).

TABLE 4

Overview of marker scores on individual plants

| | Markers linked to large introgression fragment | | | | Markers linked to small introgression fragment | | | | | |
|---|---|---|---|---|---|---|---|---|---|---|
| | P31/ M48-186 | P32/ M62-322 | P32/ M62-079 | P33/ M32-115 | P33/ M32-155 | P45/ M35-062 | P32/ M62-061 | P33/ M32-151 | P35/ M51-330 | P43/ M35-190 |
| 2348-1 | + | + | + | + | + | + | + | + | + | + |
| 2348-3 | + | + | + | + | + | + | + | + | + | + |
| 2348-4 | x | x | x | x | x | x | x | x | x | x |
| 2348-5 | x | x | x | x | x | x | x | x | x | x |
| 2348-6 | + | + | + | + | + | + | + | + | + | + |
| 2348-7 | + | + | + | + | + | + | + | + | + | + |
| 2348-8 | + | + | + | + | + | + | + | + | + | + |
| 2348-11 | x | x | x | x | x | x | x | x | x | x |
| 2348-13 | + | + | + | + | + | + | + | + | + | + |
| 2348-14 | + | + | + | + | + | + | + | ? | + | + |
| 2348-15 | + | + | ? | + | + | + | + | + | + | + |
| 2348-16 | + | + | + | + | + | + | + | + | + | + |
| 2348-18 | + | + | + | + | + | + | + | + | + | + |
| 2348-19 | – | + | + | + | + | x | + | – | + | + |
| 3591-3 | x | x | x | x | x | x | x | x | x | x |
| 3591-1 | – | – | – | – | + | + | + | + | + | + |
| *A. roylel* | + | + | + | + | + | + | + | + | + | + |
| *A. cepa* A | – | – | – | – | – | – | – | – | – | – |
| *A. cepa* B | – | – | – | – | – | – | – | – | – | – |
| *A. cepa* C | – | – | – | – | – | – | – | – | – | – |
| *A. cepa* D | – | – | – | – | + | + | – | – | – | – |

+ = AFLP ™ fragment present,
– = AFLP ™ fragment absent,
x = no good product generated,
? = not scorable.

Discussion and Conclusion:

To identify markers associated with the *Peronospora destructor* resistance locus in onion, and especially to obtain markers which are located on the smaller introgression fragment, an adapted Bulked Segregant Analysis (BSA) strategy was carried out on four individuals/pools. The BSA was carried out using a total of 96 PstI/MseI primer combinations (which were screened on four individuals/pools).

TABLE 5

Overview of marker scores on individual plants

| | Markers linked to large introgression fragment | | | | Markers linked to small introgression fragment | | | | | |
|---|---|---|---|---|---|---|---|---|---|---|
| | P31/ M48-186 | P32/ M62-322 | P32/ M62-079 | P33/ M32-115 | P33/ M32-155 | P45/ M35-062 | P32/ M62-061 | P33/ M32-151 | P35/ M51-330 | P43/ M35-190 |
| *A. cepa* 1 | | | | | | | – | – | – | – |
| *A. cepa* 2 | | | | | | | – | – | – | – |
| *A. cepa* 3 | | | | | | | – | – | – | – |
| *A. cepa* 4 | | | | | | | – | – | – | – |
| *A. cepa* 5 | | | | | | | – | – | – | – |
| *A. cepa* 6 | | | | | | | – | – | – | – |
| *A. cepa* 7 | | | | | | | – | – | – | – |
| *A. cepa* 8 | | | | | | | – | – | – | – |
| *A. cepa* 9 | | | | | | | – | – | – | – |
| *A. cepa* 10 | | | | | | | – | – | – | – |
| *A. cepa* 11 | | | | | | | – | – | – | – |
| *A. cepa* 12 | | | | | | | – | – | – | – |
| *A. cepa* 13 | | | | | | | – | – | – | – |
| *A. cepa* 14 | | | | | | | – | – | – | – |

TABLE 5-continued

Overview of marker scores on individual plants

| | Markers linked to large introgression fragment | | | | | | Markers linked to small introgression fragment | | | |
|---|---|---|---|---|---|---|---|---|---|---|
| | P31/ M48-186 | P32/ M62-322 | P32/ M62-079 | P33/ M32-115 | P33/ M32-155 | P45/ M35-062 | P32/ M62-061 | P33/ M32-151 | P35/ M51-330 | P43/ M35-190 |
| A. cepa 15 | | | | | | | − | − | − | − |
| A. cepa 16 | | | | | | | − | − | − | − |
| A. cepa 17 | | | | | | | − | − | − | − |
| A. cepa 18 | | | | | | | − | − | − | − |
| A. cepa 19 | | | | | | | − | − | − | − |
| A. cepa 20 | | | | | | | − | − | − | − |
| A. cepa 21 | | | | | | | − | − | − | − |
| A. cepa 22 | | | | | | | − | | − | − |
| A. cepa 23 | | | | | | | x | − | x | − |
| A. cepa 24 | | | | | | | − | − | − | − |

+ = AFLP ™ fragment present,
− = AFLP ™ fragment absent,
x = no good product generated,
? = not scorable.

The BSA resulted in the identification of 34 candidate markers of which 8 candidate markers were possibly positioned in the small introgression fragment. After verification, a total of four markers were identified which are located in the small introgression fragment (on which also the *Peronospora destructor* resistance locus is located).

To overcome false positive markers, the four candidate markers (P32/M62-061, P33/M32-151, P35/M51-330 and P43/M35-190) linked to the small introgression fragment were checked on 24 extra *Allium cepa* individuals. The obtained marker scores are in accordance with the expected score. Therefore, these markers are found to be linked to the small introgression fragment of interest and can be used for further selection procedures.

TABLE 6

Nomenclature of AFLP ™ primer enzyme combination

| extension | primercode |
|---|---|
| AAA | 31 |
| AAC | 32 |
| AAG | 33 |
| AAT | 34 |
| ACA | 35 |
| ACC | 36 |
| ACG | 37 |
| ACT | 38 |
| AGA | 39 |
| AGC | 40 |
| AGG | 41 |
| AGT | 42 |
| ATA | 43 |
| ATC | 44 |
| ATG | 45 |
| ATT | 46 |
| CAA | 47 |
| CAC | 48 |
| CAG | 49 |
| CAT | 50 |
| CCA | 51 |
| CCC | 52 |
| CCG | 53 |
| CCT | 54 |
| CGA | 55 |
| CGC | 56 |
| CGG | 57 |
| CGT | 58 |
| CTA | 59 |
| CTC | 60 |

TABLE 6-continued

Nomenclature of AFLP ™ primer enzyme combination

| extension | primercode |
|---|---|
| CTG | 61 |
| CTT | 62 |
| GAA | 63 |
| GAC | 64 |
| GAG | 65 |
| GAT | 66 |
| GCA | 67 |
| GCC | 68 |
| GCG | 69 |
| GCT | 70 |
| GGA | 71 |
| GGC | 72 |
| GGG | 73 |
| GGG | 73 |
| GGT | 74 |
| GTA | 75 |
| GTC | 76 |
| GTG | 77 |
| GTT | 78 |
| TAA | 79 |
| TAC | 80 |
| TAG | 81 |
| TAT | 82 |
| TCA | 83 |
| TCC | 84 |
| TCG | 85 |
| TCT | 86 |
| TGA | 87 |
| TGC | 88 |
| TGG | 89 |
| TGT | 90 |
| TTA | 91 |
| TTC | 92 |
| TTG | 93 |
| TTT | 94 |

Example 5 determination of the presence, in a plant of *Allium* genus, of an introgression fragment of *A. roylei* conferring resistance to downy mildew of onion, which can be present homozygously without causing lethality.

In a first step, the presence of Pd resistance locus to downy mildew of onion is assayed in the plant under examination. The presence of said locus can be assayed using AFLP™ technique, as exemplified in the preceding example or by assaying the resistance of the plant to natural or artificial inoculations by *Peronospora destructor*.

If the plant possesses in its genome a Pd resistance locus, the homologues of chromosome 3 of said plant necessarily correspond to one of the 4 possibilities depicted in FIG. 1 (with and without linkage to lethal sequences).

In order to distinguish the first three genomes, which are part of the present invention, from the fourth, self-pollination of the plant under examination is carried out. The progeny of the self-pollination is then examined for the presence of the Pd resistance locus. As can been seen from FIG. 1, only the first three genomes give a progeny which is theoretically at least 75% resistant, whereas the fourth depicted genome, which is not part of the present invention, gives a progeny which is less than 67% resistant to downy mildew of onion.

Knowing the percentage of resistant progeny after self-pollination, it is thus possible to deduce whether the tested plant is in one of the first three categories depicted or is in the fourth, i.e. whether or not it is in the scope of the present invention.

Example 6

Plants from the line 3591, similar to 3591-1 in the respect that they are all homozygous resistant, and having the two small introgression fragments bearing the resistance locus are crossed with a hybrid in a three way breeding scheme (wherein the three way cross has a single cross as the female parent and the plants from the 3591 line as the male parent).

The hybrid resulting from this cross, 37-1001 has been trialed in fields. This hybrid is a mid-early extreme long day type of onion, suitable for mid long storage. It shows a medium strong foliage vigour, a very uniform fall over, uniform round-flat round shaped bulbs (3.8 units/he.), a good yield potential, good skins with yellow-brown colour, a good firmness (3.4 mm). Field test data are shown in table 7, comparing 37-1001 with Tasco and Drago, two commercialized onion hybrids from Nickerson Zwaan. As can be seen from this table, the features of agronomical interest are similar in all plants.

Most important to the present invention, in disease field tests held for 2 years consecutively in 2 replications, all the tested plants 37-1001 are resistant, whereas a variety used as susceptible check, Staccato (Nickerson Zwaan hybrid), has 100% plants infected with downy mildew.

TABLE 7

| Name | Leaf colour (1 = light green, 5 = dark green) | Erectness of leaves (1 = horizontal, 5 = upright) | Leaf vigour (1 = weak growing leaves, 5 = vigourous leaves) | Leaf tips (1 = yellow or brown leaf tips, 5 = healthy green leaf tips) | Number of bolters (=plants producing a flower stem) | % of bolters (on total number of plants) | Relative earliness (measuring via timing of fall-over of leaves) | Yield (per square meter) |
|---|---|---|---|---|---|---|---|---|
| Tasco | 3 | 3 | 5 | 3 | 4 | 1.0 | 131.8 | 8.883 |
| Tasco | 3 | 3 | 5 | 3 | 7 | 1.8 | 115.5 | 8.610 |
| Tasco | 3 | 3 | 5 | 3 | 10 | 2.8 | 113.7 | 8.467 |
| Tasco | 3 | 3 | 4 | 3 | 2 | 0.6 | 133.6 | 8.028 |
| Average: Tasco | 3 | 3 | 5 | 3 | 6 | 2 | 124 | 8.50 |
| Drago | 4 | 3 | 4 | 3 | 1 | 0.3 | 97.5 | 7.640 |
| drago | 3 | 3 | 3 | 3 | 3 | 0.8 | 113.7 | 7.971 |
| drago | 5 | 3 | 4 | 3 | 3 | 0.8 | 79.4 | 7.694 |
| drago | 4 | 3 | 5 | 3 | 7 | 1.9 | 115.5 | 8.126 |
| Average: Drago | 3 | 3 | 5 | 3 | 4 | 1 | 106 | 7.99 |
| 37-1001 | 3 | 3 | 4 | 3 |  | 0.0 | 115.5 | 8.657 |
| 37-1001 | 3 | 3 | 4 | 3 | 1 | 0.3 | 97.5 | 8.622 |
| 37-1001 | 3 | 3 | 4 | 3 | 2 | 0.5 | 113.7 | 8.114 |
| 37-1001 | 3 | 3 | 5 | 3 |  | 0.0 | 115.5 | 8.852 |
| Average: 37-1001 | 3 | 3 | 5 | 3 | 2 | 0.4 | 109.6 | 8.446 |

| Name | Relative yield (100 = trial average) | Average bulb weight (g) | % of skinless bulbs | Relative % of skin retaining bulbs | Skin quality (1 = no papery skins around bulb, 9 = a lot of papery skins) | Firmness (=mm of deformation when compressed, so the lower the better) | Number of rings counted when bulb is cut |
|---|---|---|---|---|---|---|---|
| Tasco | 106.5 | 130 | 10.6 | 92.9 | 6 | 3.61 | 4.96 |
| Tasco | 103.4 | 122 | 6.0 | 97.7 | 6 | 3.62 | 5.24 |
| Tasco | 101,6 | 128 | 4.9 | 98.8 | 7 | 3.51 | 5.32 |
| Tasco | 96.4 | 124 | 12.3 | 91.1 | 6 | 3.60 | 4.08 |
| Average: Tasco | 102 | 126 | 8 | 95 | 6 | 4 | 5 |
| Drago | 91.7 | 119 | 4.5 | 99.2 | 7 | 3.38 | 5.16 |
| drago | 95.7 | 111 | 5.4 | 98.3 | 6 | 2.93 | 4.42 |
| drago | 92.4 | 118 | 3.3 | 100.5 | 7 | 3.08 | 4.63 |
| drago | 97.6 | 125 | 6.8 | 96.9 | 6 | 3.26 | 4.68 |
| Average: Drago | 96 | 120 | 6 | 98 | 6 | 3 | 5 |
| 37-1001 | 103.9 | 129 | 13.6 | 89.8 | 5 | 3.57 | 4.20 |
| 37-1001 | 103.5 | 124 | 6.3 | 97.4 | 6 | 3.17 | 4.36 |
| 37-1001 | 97.4 | 117 | 8.3 | 95.3 | 6 | 3.19 | 4.46 |
| 37-1001 | 106.3 | 122 | 11.8 | 91.7 | 6 | 3.22 | 4.92 |
| Average: 37-1001 | 101.4 | 122 | 9.1 | 94.4 | 6 | 3.28 | 4.54 |

Example 7

In the following, line 3591 or plants 3591 are homozygous resistant plants bearing the small introgression fragment, they are all plants similar to 3591-1 because they also contain the small introgression fragment in a homozygous condition and belong to the same breeding line.

3591 plants have also been used successfully as starting material for the development of new parental breeding lines useful in producing new commercial onion hybrids, resistant to the downy mildew of onion. The 3591 plants are first crossed with an inbred onion line to produce an F1 hybrid.

Indeed, through backcrossing to other pollinator lines, the downy mildew resistance gene can be introduced into other pollinator lines of many different onion types.

A first cross is made between a resistant plant having the two small introgression fragments bearing the resistance locus and a susceptible line. This cross gives rise to hybrids (F1s) which contain the small introgression fragment heterozygously. These heterozygously resistant F1 plants are used for subsequent backcrossing with a susceptible line or the susceptible line used to produce the F1 resistant plants. Such backcross step will give rise to a population which has 50% resistant and 50% susceptible plants. This 1:1 segregation will occur with every back-cross generation due to the inheritance of the dominant Pd resistance locus. All susceptible plants can be phenotyped for downy mildew susceptibility and eliminated. New onion inbred lines usable as parent material for producing F1 hybrids are obtained through several steps of backcrossing followed by self pollination as known by a man skilled in the art.

This inheritance is confirmed by the field data; among the nine plants produced by the cross sy108a*3591, the nine plants are resistant. Similarly, among the four plants produced by the cross fra*3591, all four plants are resistant. Also similarly all the 3 plants produced from the cross syt*3591 are resistant to the downy mildew of onion. These plants are then backcrossed as mentioned hereunder.

Example 8

All plants can also be genotyped with the markers disclosed in the present invention; among the 16 F1 hybrids produced when crossing 3591 plants having the two small introgression fragments bearing the resistance locus with various other inbred parental lines, all showed the expected 61 nucleotide fragment when the pair of primers (A) was used (marker P32/M62-061 linked to the small introgression fragment) and did not show the 79 nucleotide fragment usually highlighting the presence of the large introgression fragment when the marker P32/M62-079 is used (the pair of primers (B')).

REFERENCES

1. Meer, Q. P. van der and Vries, J. N. De, An interspecific cross between *Allium roylei* Stearn and *Allium cepa* L, and its backcross to *A. cepa*. Euphytica 47:29-31, 1990.
2. Kofoet, A. et al. Inheritance of resistance to Downy Mildew (Peronospora destructor [Berk.] Casp.) from *Allium roylei* Stearn in the Backcross *Allium cepa* L.*(*A. roylei*A. cepa*). Plant Breeding 105:144-149, 1990.
3. Vries, J. N. De et al. Linkage of downy mildew resistance genes Pd1 and Pd2 from *Allium roylei* Stearn in progeny of its interspecific hybrid with onion (*A. cepa* L.). Euphytica 64:131-137, 1992.
4. Vos, P. et at. AFLP: a new technique for DNA fingerprinting. Nucleic Acids Research. Vol 21, 21: 4407-4414, 1995.
5. Mukerji, K. G. *Peronospora destructor*. CMI Description of Pathogenic fungi and Bacteria No 456, 1975.
6. Viranyi, F. Downy Mildew of Onion. D M Spencer, The Downy Mildews. Chap. 21:461-15 471, 1981.
7. Hildebrand, P. D., and Sutton, J. C. Maintenance of *Peronospora destructor* in onions sets. Canadian Journal of Plant Pathology 2:239-240, 1980.
8. Vries, J. N. De. Onion chromosome nomenclature and homoeology relationships-workshop report. Euphytica 49:1-3, 1990.
9. Khrustaleva, L. I. and Kik, C. Cytogenetical studies in the bridge cross *Allium cepa**(*A. fistulosum**A. roylei*. Theor. Appl. Genet. 96: 8-14, 1998.
10. Khrustaleva, L. I. and Kik, C. Introgression of *Allium fistulosum* into *A. cepa* mediated by *A. roylei*. Theor. Appl. Genet. 100: 17-26, 2000.
11. Michelmore, R. W. et al. Identification of markers linked to disease-resistance genes by bulked segregant analysis: A rapid method to detect markers in specific genomic regions by using segregating populations. Proc. Natl. Acad. Sci. USA. 88: 9828-9832, 1991.
12. Kalkman, E. R. Analysis of the C-banded karyotype of *Allium cepa* L. Standard system of nomenclature and polymorphism. Genetica 65:141-148, 1984.
13. Rogers and Bendich. In: Gelvin S B, Schilperoort R A (eds) Plant Molecular Biology manual A6, Kluwer Academic Publ., Dordrecht, the Netherlands; 1-10, 1998.

---

The invention claimed is:

1. An onion or shallot plant of *Allium cepa* species which is resistant to downy mildew of onion caused by the fungus *Peronospora destructor* (Pd), which plant comprises a Pd resistance locus, conferring resistance to downy mildew of onion, present homozygously in the long arm of chromosome 3 in the genome of said plant, wherein the Pd resistance locus comprises (i.) a 61 nucleotide amplification product with the selective amplification primers 5'-GACTGCGTACATC-CAGAAC (SEQ ID NO:5) and 5'-GATGAGTCCT-GAGTAACTT (SEQ ID NO:6), or (ii.) a 151 nucleotide amplification product with the selective amplification primers 5'-GACTGCGTA-CATGCAGAAG (SEQ ID NO:7) and 5'-GAT-GAGTCCTGAGTAAAAC (SEQ ID NO:8), or (iii.) a 330 nucleotide amplification product with the selective amplification primers 5'-GACTGCGTA-CATGCAGACA (SEQ ID NO:9) and 5'-GAT-GAGTCCTGAGTAACCA (SEQ ID NO:10), in the genome of said plant restricted with restriction enzymes PstI and MseI; and ligated with the following oligonucleotide adapters:

```
alpha 5'-CTCGTAGACTGCGTACATGCA    (SEQ ID NO: 1)
              CATCTGACGCATGT-5',   (SEQ ID NO: 2)
       and beta  5'-GACGATGAGTCCTGAG         (SEQ ID NO: 3)
              TACTCAGGACTCAT-5';   (SEQ ID NO: 4).
```

2. The onion or shallot plant of *Allium cepa* species according to claim 1, wherein said Pd resistance locus present in the genome of said plant is a locus naturally occurring in the genome of *Allium roylei*.

3. The plant according to claim 1, wherein said Pd resistance locus is on an introgression fragment from *Allium roylei*.

4. The plant according to claim 3, wherein there is no other introgression fragment from *Allium roylei* except in the long arm of chromosome 3.

5. The plant according to claim 3, wherein said introgression fragment is less than 44% of the total length of the long arm of chromosome 3.

6. An onion or shallot plant of *Allium cepa* species, which is resistant to downy mildew of onion caused by the fungus *Peronospora destructor* (Pd), which plant comprises a Pd resistance locus, conferring resistance to downy mildew of onion, present in the long arm of at least one of the homologues of chromosome 3 in the genome of said plant, wherein any chromosomal fragment of said chromosome 3 comprising the Pd resistance locus, when present homozygously in progeny, is not lethal to said progeny, and wherein the Pd resistance locus comprises (i.) a 61 nucleotide amplification product with the selective amplification primers

```
(A)
5'-GACTGCGTACATGCAGAAC      (SEQ ID NO: 5)
and

5'-GATGAGTCCTGAGTAACTT,     (SEQ ID NO: 6)
or
```

(ii.) a 151 nucleotide amplification product with the selective amplification primers 5'-GACTGCGTACATGCAGAAG (SEQ ID NO:7) and 5'-GATGAGTCCTGAGTAAAAC (SEQ ID NO:8), or (iii.) a 330 nucleotide amplification product with the selective amplification primers 5'-GACTGCGTACATGCAGACA (SEQ ID NO:9) and 5'-GATGAGTCCTGAGTAACCA (SEQ ID NO:10), in the genome of said plant restricted with restriction enzymes PstI and MseI; and ligated with the following oligonucleotide adapters:

```
alpha 5'-CTCGTAGACTGCGTACATGCA  (SEQ ID NO: 1)

CATCTGACGCATGT-5', (SEQ ID NO: 2)
and beta 5'-GACGATGAGTCCTGAG        (SEQ ID NO: 3)

TACTCAGGACTCAT-5'. (SEQ ID NO: 4)
```

7. The plant according to claim 1, wherein the Pd resistance locus comprises a 61 nucleotide amplification product with the selective amplification primers 5'-GACTGCGTACATGCAGAAC (SEQ ID NO:5) and 5'-GATGAGTCCTGAGTAACTT (SEQ ID NO:6) in the genome of said plant restricted with the restriction enzymes PstI and MseI; and ligated with the following oligonucleotide adapters:

```
alpha 5'-CTCGTAGACTGCGTACATGCA  (SEQ ID NO: 1)

CATCTGACGCATGT-5', (SEQ ID NO: 2)
and beta 5'-GACGATGAGTCCTGAG        (SEQ ID NO: 3)

TACTCAGGACTCAT-5.  (SEQ ID NO: 4)
```

8. The plant according to claim 1, wherein the Pd resistance locus comprises a 151 nucleotide amplification product with the selective amplification primers 5'-GACTGCGTACATGCAGAAG (SEQ ID NO:7) and 5'-GATGAGTCCTGAGTAAAAC (SEQ ID NO:6) in the genome of said plant restricted with the restriction enzymes PstI and MseI; and ligated with the following oligonucleotide adapters:

```
alpha 5'-CTCGTAGACTGCGTACATGCA  (SEQ ID NO: 1)

CATCTGACGCATGT-5', (SEQ ID NO: 2)
``` and

```
beta 5'-GACGATGAGTCCTGAG        (SEQ ID NO: 3)

TACTCAGGACTCAT-5'. (SEQ ID NO: 4)
```

9. The plant according to claim 1, wherein the Pd resistance locus comprises a 330 nucleotide amplification product with the selective amplification primers 5'-GACTGCGTACATGCAGACA (SEQ ID NO:9) and 5'-GATGAGTCCTGAGTAACCA (SEQ ID NO:10) in the genome of said plant restricted with the restriction enzymes PstI and MseI; and ligated with the following oligonucleotide adapters:

```
alpha 5'-CTCGTAGACTGCGTACATGCA  (SEQ ID NO: 1)

CATCTGACGCATGT-5', (SEQ ID NO: 2)
and beta 5'-GACGATGAGTCCTGAG        (SEQ ID NO: 3)

TACTCAGGACTCAT-5'. (SEQ ID NO: 4)
```

10. A method for the production of a plant of the *Allium cepa* species which is resistant to downy mildew of onion caused by the fungus *Peronospora destructor* (Pd) comprising:

a) Obtaining an *Allium roylei* resistant to downy mildew of onion;
b) Making a interspecific cross between said *Allium roylei* and an *Allium cepa*;
c) Selecting an interspecific hybrid resistant to downy mildew of onion;
d) Backcrossing said hybrid with plant of *Allium cepa*;
e) Selecting plants resistant to downy mildew of onion;
f) Self-pollinating the resistant plant obtained at step e);
g) Selecting plants homozygously resistant to downy mildew of onion;

wherein in steps c), e) and/or g) selection of plants resistant to downy mildew of onion is carried out using the following process:

(i.) restricting the genomic DNA from said plant with restriction enzymes PstI and MseI to obtain fragments;

(ii.) ligating to such fragments the following oligonucleotide adapters:
alpha 5'-CTCGTAGACTGCGTACATGCA (SEQ ID NO:1) CATCTGACGCATGT-5' (SEQ ID NO:2), and
beta 5'-GACGATGAGTCCTGAG (SEQ ID NO:3) TACTCAGGACTCAT-5' (SEQ ID NO:4); and (iii.) selectively amplifying the resulting sets of restriction fragments with at least one of the following pairs of primers:

(A) 5'-GACTGCGTACATGCAGAAC (SEQ ID NO:5) and 5'-GATGAGTCCTGAGTAACTT (SEQ ID NO:6);

(B) 5'-GACTGCGTACATGCAGAAG (SEQ ID NO:7) and 5'-GATGAGTCCTGAGTAAAAC (SEQ ID NO:8); and/or (C) 5'-GACTGCGTACATGCAGACA (SEQ ID NO:9) and 5'-GATGAGTCCTGAGTAACCA (SEQ ID NO:10).

11. The method of claim 10 further comprising crossing the plant homozygously resistant obtained in step g) with a downy mildew susceptible plant of *Allium cepa* species.

12. The method according to claim 10, wherein, as a negative control, the amplification is also carried out with at least one of the following pairs of primers:

```
(A')
5'-GACTGCGTACATGCAGAAG
and

5'-GATGAGTCCTGAGTAAAAC;

(B')
5'-GACTGCGTACATGCAGAAC
and

5'-GATGAGTCCTGAGTAACTT;
and/or (C')
5'-GACTGCGTACATGCAGAAA
and

5'-GATGAGTCCTGAGTAACAC.
```

13. An *Allium* plant obtained by the method according to claim 10.

14. An hybrid *Allium cepa* plant obtained by crossing a downy mildew susceptible *Allium cepa* parental line with the plant of claim 1, wherein the hybrid plant comprises the Pd resistance locus.

15. The hybrid *Allium cepa* plant according to claim 14, wherein the parental line is a cytoplasmic male sterile *Allium cepa* inbred line.

16. The plant according to claim 1, wherein said plant is a cultivated onion or shallot.

17. The plant according to claim 14, wherein said plant is a cultivated onion or shallot.

18. Progeny of the plant according to claim 1, which is resistant to downy mildew of onion caused by the fungus *Peronospora destructor* (Pd)
wherein the Pd resistance locus comprises
(i.) a 61 nucleotide amplification product with the selective amplification primers 5'-GACTGCGTACATGCAGAAC (SEQ ID NO:5) and 5'-GATGAGTCCTGAGTAACTT (SEQ ID NO:6);
(ii.) a 151 nucleotide amplification product with the selective amplification primers 5'-GACTGCGTACATGCAGAAG (SEQ ID NO:7) and 5'-GATGAGTCCTGAGTAAAAC (SEQ ID NO:8); or
(iii.) a 330 nucleotide amplification product with the selective amplification primers 5'-GACTGCGTACATGCAGACA (SEQ ID NO:9) and 5'-GATGAGTCCTGACTAACCA (SEQ ID NO:10),
in the genome of said plant restricted with restriction enzymes PstI and MseI; and ligated with the following oligonucleotide adapters:

```
alpha 5'-CTCGTAGACTGCGTACATGCA    (SEQ ID NO: 1)

CATCTGACGCATGT-5',    (SEQ ID NO: 2)
and beta  5'-GACGATGAGTCCTGAG        (SEQ ID NO: 3)

TACTCAGGACTCAT-5'.    (SEQ ID NO: 4)
```

19. Bulb or seed of the plant according to claim 1.
20. Bulb or seed of the plant according to claim 6.
21. Bulb or seed of the plant according to claim 14.

* * * * *